United States Patent [19]
Saxon et al.

[11] Patent Number: 6,030,830
[45] Date of Patent: Feb. 29, 2000

[54] IMMUNOGLOBULIN TRANS-SPLICED TRANSCRIPTS AND USES THEREOF

[75] Inventors: Andrew Saxon, Santa Monica; Ke Zhang, Los Angeles, both of Calif.; Shigeharu Fujieda, Fukui, Japan

[73] Assignee: The Regents of the University of California, Oakland, Calif.

[21] Appl. No.: 08/911,894

[22] Filed: Aug. 15, 1997

Related U.S. Application Data

[60] Provisional application No. 60/023,579, Aug. 19, 1996.

[51] Int. Cl.[7] .......................... C12N 15/11; C12N 15/63; C07H 21/04
[52] U.S. Cl. ................... 435/320.1; 536/23.1; 536/24.1; 536/24.31
[58] Field of Search .............................. 435/6, 69.1, 69.7, 435/172.3, 328, 372.3, 320.1, 375; 530/387.3, 387.1; 536/23.1, 23.4, 24.1, 24.31, 24.33, 24.5; 514/44

[56] References Cited

PUBLICATIONS

Branch. TIBS. 23, 45–50 (Feb. 1998).
Gewirtz et al. PNAS. 93. 3161–3163 (Apr. 1996).
Rojanasakul. 18. 115–131 (Jan. 1996).
Mastrangelo et al. Seminars in Oncology 23, 4–21 (Feb. 1996).
Golub. The Cellular Basis of the Immune Response. pp. 197–203 (1981).
Berdoz, et al., "Specific Amplification By PCR of Rearranged Genomic Variable Regions of Immunoglobulin Genes From Mouse Hybidoma Cells," *Research*, 4(5) :256–264, 1995.
Bottaro, et al., "S Region Transcription per se Promotes Basal IgE Class Switch Recombination But Additional Factors Regulate the Efficiency of the Process," *EMBO Journal*, 13(3) :665–674, 1994.
Chan, et al., "Expression of IgE From A Nonrearranged ε Locus In Cloned B–Lymphoblastoid Cells That Also Express IgM," *Journal of Immun.*, 144(9) :3563–3568, May 1990.
Chen, et al., "Double Isotype Production By A Neoplastic B Cell Line. Allelically Excluded Production of $\mu$ and $\gamma 1$ Heavy Chains Without $C_h$ Gene Rearrangement," *J. Exp. Med.*, 164:562–579, Aug. 1986.
Cheong, C., & P.B. Moore, "Solution Structure of An Unusually Stable RNA Tetraplex Containing G– and U–Quartet Structures," *Biochemistry*, 31:8406–8414, 1992.
Chiara, M.D., & R. Reed, "A Two–Step Mechanism for 5| and 3| Splice–Site pairing," *Nature*, 375:510–513, Jun. 1995.
Diaz–Sanchez, et al., "Diesel Exhaust Particles Induce Local IgE Production in Vivo and After the Pattern of IgE Messenger RNA Isoforms," *J. Clin. Invest.*, 94:1417–1425, Oct. 1994.

Ellison, J., & L. Hook, "Linkage and Sequence Homology of Two Human Immunoglobulin γ Heavy Chain Constant Region Genes," *proc. Natl. Acad. Sci. USA*, 79:1984–1988, Mar. 1982.
Fujieda, et al., "Multiple Types of Chimeric Germ–Line Ig Heavy–Chain Transcripts in Human B Clls: Evidence for Trans–Splicing of Human Ig RNA," *Journal of Immun.*, 157:3450–3459, 1996.
Fujieda, et al., "IL–4 Plus CD40 Monoclonal Antibody Induces Human B Cells γ Subclass–Specific Isotype Switch: Switching to γ1, γ3, and γ4, But Not γ2," *J. of Immun.*, 2318–2328, 1995.
Gaff, C., & S. Gerondakis, "RNA Splicing Generates Alternate Forms of Germline Immunoglobulin α Heavy Chain Transcripts,"*Int. Immun.*, 2(12) :1143–1148, 1990.
Gerstein, et al., "Isotype Switching of An Immunoglobulin Heavy Chain Transgene Occurs By DNA Recombination Between Different Chromosomes," *Cell*, 63:537–548, Nov. 1990.
Han, et al., "Regulated Expression of Immunoglobulin Trans–mRNA Consisting of the Variable Region of a Transenic $\mu$ Chain and Constant Regions of Endogenous Isotypes," *International Immunology*, 3(12) :1197–1206, Aug. 1991.
Harriman, et al, "Immunoglobulin Class Switch Recombination," *Annu. Rev. Immunol.*, 11:361–384, 1993.
Harriman, et al., "Class Switch in Iα Exon–Deficient Mice," *J. Clin. Invest.*, 97(2) :477–485, Jan. 1996.
Jung, et al., "Shutdown of Class Switch Recombination By Deletion of a Switch Region Control Element," *Science*, 259:984–987, Feb. 1993.
Kim, et al., "Probing the Structure of a Putative Intermediate in Homologous Recombination: The Third Strand in the Parallel DNA Triplex is in Contact With the Major Groove of the Duplex," *J. Mol. Biol.*, 247:874–889, 1995.
Kim, et al., "Tetramerization of An RNA Oligonucleotide Containing a GGGG Sequence," *Nature*, 351:331–332, May 1991.
Kitani, A., & W. Strober, "Regulation of Cγ Subclass Germ–Line Transcripts in Human Peripheral Blood B Cells," *J. of Immun.*, 151(7) :3478–3488, Oct. 1991.
Knight, et al., "Transchromosomally Derived Ig Heavy Chains," *J. of Immun.*, 684–691, 1995.

(List continued on next page.)

*Primary Examiner*—John L. LeGuyader
*Assistant Examiner*—Mark L. Shibuya
*Attorney, Agent, or Firm*—Mandel & Adriano

[57] ABSTRACT

Compositions and methods for directing the synthesis of a particular human immunoglobulin isotype are provided. Nucleic acid molecules representing sense and antisense sequences of trans-spliced messenger ribonucleic acid molecules enhance or reduce, respectively, isotype recombination to IgE, IgA or IgG isotypes from an IgM isotype. Particular methods and compositions for the treatment of allergy and allergic reaction are described through inhibition of IgE.

5 Claims, 2 Drawing Sheets

OTHER PUBLICATIONS

Kumimoto, et al., "Molecular Analysis of Double Isotype Expression in IgA Switching," *Journal of Immun.*, 150(4) : 1338–1347, Feb. 1991.

Li, et al., "Expression of $I_\mu$–$C_\gamma$ Hybrid Germline Transcripts Subsequent to Immunoglobulin Heavy Chain Class Switching," *Int. Immun.*, 6(4) :491–497, 1993.

Lorenz, et al., "Switch Transcripts in Immunoglobulin Class Switching," *Science*, 267:1825–1828, Mar. 1995.

Lutzker, S., & F.W. Alt, "Structure and Expression of Germ Line Immunoglobulin γ2b Transcripts," *Molecular & Cellular Biology*, 8(4) :1849–1852, Apr. 1988.

Lutzker, et al., "Mitogen– and IL–4–Regulated Expression of Germ–Line Ig γ2b Transcripts: Evidence for Directed Heavy Chain Class Switching," *Cell*, 53:177–184, Apr. 1988.

MacKenzie, T., & H.M.Dosch, "Clonal and Molecular Characteristics of the Human IgE–Committed B Cell Subset," *J. Exp. Med.*, 169:407–430, Feb. 1989.

Kinashi, et al., "Human Neoplastic B Cells Express More Than Two Isotypes of Immunoglobulins Without Deletion of Heavy–Chain Constant–Region Genes," *Genes & Development*, 1:465–470, 1987.

Max, et al., "Duplication and Deletion in the Human Immunoglobulin ϵ Genes," *Cell*, 29:691–699, 1982.

Mills, et al., "Sequences of Human Immunoglobulin Switch Regions: Implications For Recombination and Transcription," *Nucleic Acids Res.*, 18(24) :7305–7316, 1990.

Morgan, A. Richard, "Three–Stranded (triplex) DNAs (RNAs) : Do they Have a Role in Biology?" *Indian J. of Biochem. & Biophysics*, 31:83–87, Apr. 1994.

Neale, G.A.M., & G.R. Kitchingman, "mRNA Transcripts Initiating Within the Human Immunoglobulin mu Heavy Chain Enhancer Region Contain a Non–Translatable Exon and Are Extremely Heterogeneous at the 5 | End," *Nucleic Acids Res.*, 19(9) :2427–2433, 1991.

Nolan–Willard, et al., "Coexpression of μ and γ1 Heavy Chains Can Occur by a Discontinuous Transcription Mechanism From the Same Unrearranged Chromosome," *Proc. Natl. Acad. Sci. USA*, 89:1234–1238, Feb. 1992.

Perlmutter, A.P., & W. Gilbert, "Antibodies of the Secondary Response Can Be Expressed Without Switch Recombination in Normal Mouse B Cells," *Proc. Natl. Sci. USA*, 81:7189–7193, Nov. 1984.

Ravetch, et al., "Structure of the Human Immunoglobulin μ Locus: Characterization of Embryonic and Rearranged J and D Genes," *Cell*, 27:583–591, Dec. 1991.

Rothman, et al., "Structure and Expression of Germ Line Immunoglobulin Heavy–Chain ϵ Transcripts: Interleukin–4 Plus Lipopolysaccharide–Directed Switching to Cϵ," *Molecullar & Cellular Biology*, 10(4) :1672–1679, Apr. 1990.

Sen, D., & W. Gilbert, "A Sodium–Potassium Switch in the Formation of Four–Stranded G4–DNA," *Nature*, 344:410–414, Mar. 1990.

Shapira, et al., "Deletional Switch Recombination Occurs in Interleukin–4–Induced Isotype Switching to IgE Expression by Human B Cells," *Proc. Natl. Acad. Sci. USA*, 88:7528–7532, Sep. 1991.

Shimizu, et al., "Immunoglobulin Double–Isotype Expression by Trans–mRNA in a Human Immunoglobulin Transgenic Mouse," *Proc. Natl. Acad. Sci. USA*, 86:8020–8023, Oct. 1989.

Shimizu, et al., "Trans–Splicing As a Possible Molecular Mechanism for the Multiple Isotype Expression of the Immunoglobulin Gene," *J. Exp. Med.*, 173:1385–1393, Jun. 1991.

Shimizu, A., & T. Honjo, "Synthesis and Regulation of Trans–mRNA Encoding the Immunoglobulin 1 Heavy Chain," *FASEB J.*, 7:149–154, Jan. 1993.

Sideras, et al., "Production of Sterile Transcripts of Cγ Genes In An IgM–Producing Human Neoplastic B Cell Line That Switches To IgG–Producing Cells," *International Immun.*, 1(6) :631–642, Oct. 1989.

Sklenar, V., & J. Feigon, "Formation of a Stable Triplex From a Single DNA Strand," *Nature*, 345:836–838, Jun. 1990.

Stavnezer, et al., "Immunoglobulin Heavy–Chain Switching May Be Directed By Prior Indction of Transcripts From Constant–Region Genes," *Proc. Natl. Acad. Sci. USA*, 85:7704–7708, Oct. 1988.

Stavnezer–Nordgren, J., & S. Sirlin, "Specificity of Immunoglobulin Heavy Chain Switch Correlates With Activity of Germline Heavy Chain Genes Prior to Switching," *EMBO Journal*, 5(1) :95–102, 1986.

Van Meervelt, et al., "High–Resolution Structure of a DNA Helix Forming (C=G) *G Base Triplets," *Nature*, 374:742–744, 1995.

Xu, et al., "Replacement of Germ–Line ϵ Promoter By Gene Targeting Alters Control of Immunoglobulin Heavy Chain Class Switching," *Proc. Natl. Acad. Sci. USA*, 90:3705–3709, Apr. 1993.

Yaoita, et al., "Expression of Lymphocyte Surface IgE Does Not Require Switch Recombination," *Nature*, 297:697–699, Jun. 1982.

Zhang, et al., "Two Unusual Forms of Human Immunoglobulin E Encoded by Alternative RNA Splicing of ϵ Heavy Chain Membrane Exons," *J. Exp. Med.*, 176:233–243, Jul. 1992.

Zhang, et al., "Switch Circles From IL–4 Directed ϵ Class Switching From Human B Lymphocytes," *J. Immun.*, 3427–3435, 1994.

Zhang, et al., "A Selective Defect in IgG2b Switching as a Result of Targeted Mutation of the 1γ2b Promoter and Exon," *EMBO Journal*, 12(9) :3529–3537, 1993.

Zhurkin, et al., "A Parallel DNA Triplex As a Model for the Intermediate in Homologous Recombination," *J. Mol. Biol.*, 239:181–200, 1994.

Gauchat, et al., "Structure and Expression of Germline ϵ Transcripts in Human B Cells Induced by Interleukin 4 to Switch to IgE Production," *J. Exp. Med.*, 172:463–473, Aug. 1991.

Zhang, et al., "CD40 Stimulation Provides An IFN–γ–Independent and IL–4–Dependent Differentiation Signal Directly To Human B Cells for IgE Production," *J. of Immun.*, 146(6) :1836–1842, Mar. 1991.

SEQUENCE LISTING (1) GENERAL INFORMATION:

(iii) NUMBER OF SEQUENCES: 90

(2) INFORMATION FOR SEQ ID NO:1:

(i) SEQUENCE CHARACTERISTICS:
      (A) LENGTH: 15 base pairs (B) TYPE: nucleic acid
        (C) STRANDEDNESS: single
        (D) TOPOLOGY: linear (xi) SEQUENCE DESCRIPTION: SEQ ID NO:1:

CCGACATGCC TCCAC                                                15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2:

GTGGAGGCAT GTCGG                                                15

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:3:

CGCTTCAGGG AGTGCA                                               16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:4:

TGCACTCCCT GAAGCG                                               16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:5:

GACAGCAGGG AGTGCG                                               16

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:6:

CGCACTCCCT GCTGTC                                               16

(2) INFORMATION FOR SEQ ID NO:7:

(i) SEQUENCE CHARACTERISTICS:
        (A) LENGTH: 16 base pairs
        (B) TYPE: nucleic acid

```
        (C) STRANDEDNESS: single
        (D) TOPOLOGY: linear (xi) SEQUENCE DESCRIPTION: SEQ ID NO:7:

CCCGACATCT TCCACC                                                        16

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:8:

GGTGGAAGAT GTCGGG                                                        16

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:9:

CGCTTCAGCC TCCACC                                                        16

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:10:

GGTGGAGGCT GAAGCG                                                        16

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:11:

GACAGCAGCC TCCACA                                                        16

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:12:

TGTGGAGGCT GCTGTC                                                        16

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: single
```

(D) TOPOLOGY: linear (xi) SEQUENCE DESCRIPTION: SEQ ID NO:13:

CAGCGAGGCC TCCACA                                                    16

(2) INFORMATION FOR SEQ ID NO:14:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:14:

TGTGGAGGCC TCGCTG                                                    16

(2) INFORMATION FOR SEQ ID NO:15:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:15:

GACAGCAGCA TCCCCG                                                    16

(2) INFORMATION FOR SEQ ID NO:16:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:16:

CGGGGATGCT GCTGTC                                                    16

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:17:

TCGACTTCTG GGGCCAAGGG                                                20

(2) INFORMATION FOR SEQ ID NO:18:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:18:

ACAGTCTTAG GGAGAGTTTA TGACTGT                                        27

(2) INFORMATION FOR SEQ ID NO:19:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:19:

GGGCTTCCAA GCCAACAGGG CACGACA                                               27

(2) INFORMATION FOR SEQ ID NO:20:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:20:

TTGTCCAGGC CAGCAGCATC ACTGGA                                                26

(2) INFORMATION FOR SEQ ID NO:21:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:21:

ACTGCTCAGT GGATGGACTC ACACTCCCTT                                            30

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:22:

TTGCCTATGT GCCCCTCCTG GATGA                                                 25

(2) INFORMATION FOR SEQ ID NO:23:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:23:

ATGGGCATGG GGGACCATAT TTGGA                                                 25

(2) INFORMATION FOR SEQ ID NO:24:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:24:

GTGGGCACTC GACACAACAT TTGCG                                                 25

(2) INFORMATION FOR SEQ ID NO:25:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:25:

GACTGAAACC CGTGGCCTGG CAGATGA                                  27

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:26:

AGGCTCCACT GCCCGGCACA GAAATA                                   26

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:27:

AAGACCAAGA AGTCAGAGAC CCGACTG                                  27

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:28:

TGTCCCTTAG AGGACAGGTG GCCAAG                                   26

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:29:

CTGTGTCGGC CCAGCTTATT TCAACCAAG                                29

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:30:

TAGTGCGGTC TGTACAGCGT GGC                                      23

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:31:

```
GTTGATAGTC CCTGGGGTGT A                                              21

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:32:

TCACCAACTG GGACGACATG GAG                                            23

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:33:

ACCCTGGTCA CCGTCTCCTC A                                              21

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:34:

ACAGTCTTAG GGAGAGTTTA TGACTGT                                        27

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:35:

TTGTCCAGGC CGGCAGCATC ACCAGA                                         26

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:36:

CTCTGGCCAT CGGTGCCACC TCAG                                           24

(2) INFORMATION FOR SEQ ID NO:37:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:37:
```

```
AAGCACACGT TCCTCCTGCA GCCACACCT                                                29

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:38:

TTTTGCAGCA CTTGGCTTGT TCCCTAT                                                  27

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:39:

ATGGTCCCCC CAGGAACTCA GGT                                                      23

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:40:

ACTGACGGTC CTGCCACAGG TGGT                                                     24

(2) INFORMATION FOR SEQ ID NO:41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:41:

TCGCGCAGCC AGGACACCTG AATCT                                                    25

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:42:

AGCTGTCCAG GAACCCGACA GGGAG                                                    25

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:43:

GCAGGGCTGG CTGGTGCAGA CTGCC                                                    25
```

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:44:

CAGCTTAACT CAATCTGGAC CACCA                                    25

(2) INFORMATION FOR SEQ ID NO:45:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:45:

CATCTCAGCT GAACCAGTTT GAC                                      23

(2) INFORMATION FOR SEQ ID NO:46:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:46:

ACGGAGGTGG CATTGGAGGG AATGT                                    25

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:47:

GGACAAGTCC ACGTCCATGA                                          20

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:48:

CTCCTTAATG TCACGCACGA TTTC                                     24

(2) INFORMATION FOR SEQ ID NO:49:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:49:

CAAGGCTCGC AGTGACCAGG CGCCCGACAT GGTAAGAGAC AGGCAGCCGC CGCTGCTGCA    60

(2) INFORMATION FOR SEQ ID NO:50:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:50:

CAAGGCTCGC AGTGACCAGG CGCCCGACAT GCCTCCACAC AGAGCCCATC CGTCTTCCCC    60

(2) INFORMATION FOR SEQ ID NO:51:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:51:

GGCTGGCACT GACTAGGTTC TGTCCTCACA GCCTCCACAC AGAGCCCATC CGTCTTCCCC    60

(2) INFORMATION FOR SEQ ID NO:52:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:52:

AGGCACCAAA TGGACGACCC GGCGCTTCAG GTATCCCAGC CCACCGGAGC CCCAATCGAG    60

(2) INFORMATION FOR SEQ ID NO:53:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:53:

AGGCACCAAA TGGACAGCCC GGCGCTTCAG GGAGTGCATC CAGCCCCAAC CCTTTTCCCC    60

(2) INFORMATION FOR SEQ ID NO:54:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:54:

CCCTTTCTCT TTTGTCCTGC GGGTCCTCAG GGAGTGCATC C                       41

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:55:

GCCCCAACCC TTTTCCCC                                                  18

(2) INFORMATION FOR SEQ ID NO:56:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:56:

CCTCCTCTCA GCCAGGACCA AGGACAGCAG GTGTGCCGGG AGCAGAGCAG CGAGGGTGAG     60

(2) INFORMATION FOR SEQ ID NO:57:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:57:

CCTCCTCTCA GCCAGGACCA AGGACAGCAG GGAGTGCGTC CGCCCCAACC CTTTTCCACC     60

(2) INFORMATION FOR SEQ ID NO:58:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:58:

CCCTTTCTCT TTTGTCCTGC GGGTCCTCAG GGAGTGCATC CGCCCCAACC CTTTTCC     57

(2) INFORMATION FOR SEQ ID NO:59:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:59:

CAAGGCTCGC AGTGACCAGG CGCCCGACAT CTTCCACCAA GGGCCCATCC GTCTTCCCCC     60

(2) INFORMATION FOR SEQ ID NO:60:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:60:

CGCGGTCACA TGGCACCACC TCTCTTGCAG CTTCCACCAA GGGCCCATCC GTCTTCCCCC     60

(2) INFORMATION FOR SEQ ID NO:61:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:61:

AGGCACCAAA TGGACGACCC GGCGCTTCAG CCTCCACCAA GGGCCCAT     48

(2) INFORMATION FOR SEQ ID NO:62:

```
      (i) SEQUENCE CHARACTERISTICS:
           (A) LENGTH: 11 base pairs
           (B) TYPE: nucleic acid
           (C) STRANDEDNESS: single
           (D) TOPOLOGY: linear (xi) SEQUENCE DESCRIPTION: SEQ ID NO:62:

CGTCTTCCCC C                                                              11

(2) INFORMATION FOR SEQ ID NO:63:

(i) SEQUENCE CHARACTERISTICS:
           (A) LENGTH: 55 base pairs
           (B) TYPE: nucleic acid
           (C) STRANDEDNESS: single
           (D) TOPOLOGY: linear (xi) SEQUENCE DESCRIPTION: SEQ ID NO:63:

CCTCCTCTCA GCCAGGACCA AGGACAGCAG CATCCCCGAC CAGCCCCAAG GTCTT             55

(2) INFORMATION FOR SEQ ID NO:64:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (xi) SEQUENCE DESCRIPTION: SEQ ID NO:64:

CGCGTCCTCA CAGTGCATTC TGTGTTCCAG CATCCCCGAC CAGCCCCAAG GTCTTCCCGC         60

(2) INFORMATION FOR SEQ ID NO:65:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (xi) SEQUENCE DESCRIPTION: SEQ ID NO:65:

CCTCCTCTCA GCCAGGACCA AGGACAGCAG CCTCCACACA GAGCCCATCC GTCTTCCCCT         60

(2) INFORMATION FOR SEQ ID NO:66:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (xi) SEQUENCE DESCRIPTION: SEQ ID NO:66:

GCTGGCACTG ACTAGGTTCT GTCCTCACAG CCTCCACACA GAGCCCATCC GTCTTCCCCT         60

(2) INFORMATION FOR SEQ ID NO:67:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (xi) SEQUENCE DESCRIPTION: SEQ ID NO:67:

AGCAGGTGTG CCGGGAGCAG AGCAGCGAGG GTGAGTGTGG CAGAGGACAG AAGGGTGGAA         60

(2) INFORMATION FOR SEQ ID NO:68:
```

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:68:

AGCAGGTGTG CCGGGAGCAG AGCAGCGAGG CCTCCACACA GAGCCCATCC GTCTTCCCCT    60

(2) INFORMATION FOR SEQ ID NO:69:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:69:

GCTGGCACTG ACTAGGTTCT GTCCTCACAG CCTCCACACA GAGCCCATCC GTCTTCCCCT    60

(2) INFORMATION FOR SEQ ID NO:70:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (xi) SEQUENCE DESCRIPTION: SEQ ID NO:70:

CTACCCAGGC TCCACTGCCC GGCACAGAAA TAACAACCAC GGTTACTGAT CATCTGGGAG    60

CTGTCCAGGA ACCCGACAGG GAGCCGGACG GGCCACACCA TCCACAGGCA CCAAATGGAC   120

GACCCGGCGC TTCAG                                                   135

(2) INFORMATION FOR SEQ ID NO:71:

(i) SEQUENCE CHARACTERISTICS:
        (A) LENGTH: 644 base pairs
        (B) TYPE: nucleic acid
        (C) STRANDEDNESS: single
        (D) TOPOLOGY: linear (xi) SEQUENCE DESCRIPTION: SEQ ID NO:71:

TTTTTTAAAG TAAGATGTTT AAGAAATTAA ACAGTCTTAG GGAGAGTTTA TGACTGTATT    60

CAAAAAGTTT TTTAAATTAG CTTGTTATCC CTTCATGTGA TAACTAATCT CAAATACTTT   120

TTCGATACCT CAGAGCATTA TTTTCATAAT GAGCTGTGTT CACAATCTTT TTAGGTTAAC   180

TCGTTTTCTC TTTGTCATTA AGGAGAAACA CTTTGATATT CTGATAGAGT GGCCTTCATT   240

TTAGTATTTT TCAAGACCAC TTTTCAACTA CTCACTTTAG GATAAGTTTT AGGTAAAATG   300

TGCATCATTA TCCTGAATTA TTTCAGTTAA GCATGTTAGT TGGTGGCATA AGAGAAAACT   360

CAATCAGATA GTGCTGAGAC AGGACTGTGG AGACACCTTA GAAGGACAGA TTCTGTTCCG   420

AATCACCGAT GCGGCGTCAG CAGGACTGGC CTAGCGGAGG CTCTGGGAGG GTGGCTGCCA   480

GGCCCGGCCT GGGCTTTGGG TCTCCCCGGA CTACCCAGAG CTGGGATGCG TGGCTTCTGC   540

TGCCGGGCCG ACTGGCTGCT CAGCCCCAGC CCTTGTTAAT GGACTTGGAG GAATGATTCC   600

ATGCCAAAGC TTTGCAAGGC TCGCAGTGAC CAGGCGCCCG ACAT                   644

(2) INFORMATION FOR SEQ ID NO:72:

(i) SEQUENCE CHARACTERISTICS:
        (A) LENGTH: 1284 base pairs
        (B) TYPE: nucleic acid (C) STRANDEDNESS: single
        (D) TOPOLOGY: linear (xi) SEQUENCE DESCRIPTION: SEQ ID NO:72:

```
GCCTCCACAC AGAGCCCATC CGTCTTCCCC TTGACCCGCT GCTGCAAAAA CATTCCCTCG     60

AATGCCACCT CCGTGACTCT GGGCTGCCTG GCCACGGGCT ACTTCCCGGA GCCGGTGATG    120

GTGACCTGGG ACACAGGCTC CCTCAACGGG ACAACTATGA CCTTACCAGC CACCACCCTC    180

ACGCTCTCTG GTCACTATGC CACCATCAGC TTGCTGACCG TCTCGGGTGC GTGGGCCAAG    240

CAGATGTTCA CCTGCCGTGT GGCACACACT CCATCGTCCA CAGACTGGGT CGACAACAAA    300

ACCTTCAGCG TCTGCTCCAG GGACTTCACC CCGCCCACCG TGAAGATCTT ACAGTCGTCC    360

TGCGACGGCG GCGGGCACTT CCCCCCGACC ATCCAGCTCC TGTGCCTCGT CTCTGGGTAC    420

ACCCCAGGGA CTATCAACAT CACCTGGCTG GAGGACGGGC AGGTCATGGA CGTGGACTTG    480

TCCACCGCCT CTACCACGCA GGAGGGTGAG CTGGCCTCCA CACAAAGCGA GCTCACCCTC    540

AGCCAGAAGC ACTGGCTGTC AGACCGCACC TACACCTGCC AGGTCACCTA TCAAGGTCAC    600

ACCTTTGAGG ACAGCACCAA GAAGTGTGCA GATTCCAACC CGAGAGGGGT GAGCGCCTAC    660

CTAAGCCGGC CCAGCCCGTT CGACCTGTTC ATCCGCAAGT CGCCCACGAT CACCTGTCTG    720

GTGGTGGACC TGGCACCCAG CAAGGGGACC GTGAACCTGA CCTGGTCCCG GGCCAGTGGG    780

AAGCCTGTGA ACCACTCCAC CAGAAAGGAG GAGAAGCAGC GCAATGGCAC GTTAACCGTC    840

ACGTCCACCC TGCCGGTGGG CACCCGAGAC TGGATCGAGG GGGAGACCTA CCAGTGCAGG    900

GTGACCCACC CCCACCTGCC CAGGGCCCTC ATGCGGTCCA CGACCAAGAC CAGCGGCCCG    960

CGTGCTGCCC CGGAAGTCTA TGCGTTTGCG ACGCCGGAGT GGCCGGGGAG CCGGGACAAG   1020

CGCACCCTCG CCTGCCTGAT CCAGAACTTC ATGCCTGAGG ACATCTCGGT GCAGTTGCTG   1080

CACAACGAGG TGCAGCTTCC GGACGCCCGG CACAGCACGA CGCAGCCCCG CAAGACCAAG   1140

GGCTCCGGCT TCTTCGTCTT CAGCCGCCTT GAGGTGACCA GGGCCGAATG GGAGCAGAAA   1200

GATGAGTTCA TCTGCCGTGC AGTCCATGAG GCAGCGAGCC CCTCACAGAC CGTCCAGCGA   1260

GCGGTGTCTG TAAATCCCGG TAAA                                          1284
```

(2) INFORMATION FOR SEQ ID NO:73:

(i) SEQUENCE CHARACTERISTICS:
        (A) LENGTH: 1298 base pairs
        (B) TYPE: nucleic acid
        (C) STRANDEDNESS: single
        (D) TOPOLOGY: linear (xi) SEQUENCE DESCRIPTION: SEQ ID NO:73:

```
GGGAGTGCAT CCGCCCCAAC CCTTTTCCCC CTCGTCTCCT GTGAGAATTC CCCGTCGGAT     60

ACGAGCAGCG TGGCCGTTGG CTGCCTCGCA CAGGACTTCC TTCCCGACTC CATCACTTTC    120

TCCTGGAAAT ACAAGAACAA CTCTGACATC AGCAGCACCC GGGGCTTCCC ATCAGTCCTG    180

AGAGGGGCA AGTACGCAGC CACCTCACAG GTGCTGCTGC CTTCCAAGGA CGTCATGCAG    240

GGCACAGACG AACACGTGGT GTGCAAAGTC CAGCACCCCA ACGGCAACAA AGAAAAGAAC    300

GTGCCTCTTC CAGTGATTGC CGAGCTGCCT CCCAAAGTGA GCGTCTTCGT CCCACCCCGC    360

GACGGCTTCT TCGGCAACCC CCGCAAGTCC AAGCTCATCT GCCAGGCCAC GGGTTTCAGT    420

CCCCGGCAGA TTCAGGTGTC CTGGCTGCGC GAGGGGAAGC AGGTGGGGTC TGGCGTCACC    480

ACGGACCAGG TGCAGGCTGA GGCAAAGGAG TCTGGGCCCA CGACCTACAA GGTGACCAGC    540

CACTGACCAT CAAAGAGAGC GACTGGCTCA GCCAGAGCAT GTTCACCTGC CGGGTGGATC    600
```

```
ACAGGGGCCT GACCTTCCAG CAGAATGCGT CCTCCATGTG TGTCCCCGAT CAAGACACAG      660

CCATCCGGGT CTTCGCCATC CCCCCATCCT TTGCCAGCAT CTTCCTCACC AAGTCCACCA      720

AGTTGACCTG CCTGGTCACA GACCTGACCA CCTATGACAG CGTGACCATC TCCTGGACCC      780

GCCAGAATGG CCAAGCTGTG AAAACCCACA CCAACATCTC CGAGAGCCAC CCCAATGCCA      840

CTTTCAGCGC CGTGGGTGAG GCCAGCATCT GCGAGGATGA CTGGAATTCC GGGGAGAGGT      900

TCACGTGCAC CGTGACCCAC ACAGACCTGC CCTCGCCACT GAAGCAGACC ATCTCCCGGC      960

CCAAAGGGGT GGCCCTGCAC AGGCCCGATG TCTACTTGCT GCCACCAGCC CGGGAGCAGC     1020

TGAACTTGCG GGAGTCGGCC ACCATCACGT GCCTGGTGAC GGGCTTCTCT CCCGCGGACG     1080

TCTTCGTGCA GTGGATGCAG AGGGGGCAGC CCTTGTCCCC GGAGAAGTAT GTGACCAGCG     1140

CCCCAATGCC TGAGCCCCAG GCCCCAGGCC GGTACTTCGC CCACAGCATC CTGACCGTGT     1200

CCGAAGAGGA ATGAACACG GGGGAGACCT ACACCTGCGT GGTGGCCCAT GAGGCCCTGC     1260

CCAACAGGGT CACCGAGAGG ACCGTGGACA AGTCCACC                            1298

(2) INFORMATION FOR SEQ ID NO:74:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:74:

TAGATCACAA GCCCAGCAAC ACCAAGGT                                        28

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:75:

GCCTCCACAC AGAGCCCATC                                                 20

(2) INFORMATION FOR SEQ ID NO:76:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:76:

CGCTTCAGGG AGTGCAT                                                    17

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:77:

CGCTTCAGGG AGTGCATC                                                   18

(2) INFORMATION FOR SEQ ID NO:78:
```

(i) SEQUENCE CHARACTERISTICS:
                  (A) LENGTH: 19 base pairs
                  (B) TYPE: nucleic acid
                  (C) STRANDEDNESS: single
                  (D) TOPOLOGY: linear (xi) SEQUENCE DESCRIPTION: SEQ ID NO:78:

CGCTTCAGGG AGTGCATCC                                                    19

(2) INFORMATION FOR SEQ ID NO:79:

(i) SEQUENCE CHARACTERISTICS:
                  (A) LENGTH: 20 base pairs
                  (B) TYPE: nucleic acid
                  (C) STRANDEDNESS: single
                  (D) TOPOLOGY: linear (xi) SEQUENCE DESCRIPTION: SEQ ID NO:79:

CGCTTCAGGG AGTGCATCCA                                                   20

(2) INFORMATION FOR SEQ ID NO:80:

(i) SEQUENCE CHARACTERISTICS:
                  (A) LENGTH: 21 base pairs
                  (B) TYPE: nucleic acid
                  (C) STRANDEDNESS: single
                  (D) TOPOLOGY: linear (xi) SEQUENCE DESCRIPTION: SEQ ID NO:80:

CGCTTCAGGG AGTGCATCCA G                                                 21

(2) INFORMATION FOR SEQ ID NO:81:

(i) SEQUENCE CHARACTERISTICS:
                  (A) LENGTH: 22 base pairs
                  (B) TYPE: nucleic acid
                  (C) STRANDEDNESS: single
                  (D) TOPOLOGY: linear (xi) SEQUENCE DESCRIPTION: SEQ ID NO:81:

CGCTTCAGGG AGTGCATCCA GC                                                22

(2) INFORMATION FOR SEQ ID NO:82:

(i) SEQUENCE CHARACTERISTICS:
                  (A) LENGTH: 23 base pairs
                  (B) TYPE: nucleic acid
                  (C) STRANDEDNESS: single
                  (D) TOPOLOGY: linear (xi) SEQUENCE DESCRIPTION: SEQ ID NO:82:

CGCTTCAGGG AGTGCATCCA GCC                                               23

(2) INFORMATION FOR SEQ ID NO:83:

(i) SEQUENCE CHARACTERISTICS:
                  (A) LENGTH: 24 base pairs
                  (B) TYPE: nucleic acid
                  (C) STRANDEDNESS: single
                  (D) TOPOLOGY: linear (xi) SEQUENCE DESCRIPTION: SEQ ID NO:83:

CGCTTCAGGG AGTGCATCCA GCCC                                              24

(2) INFORMATION FOR SEQ ID NO:84:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:84:

GCGCTTCAGG GAGTGCAT                                                      18

(2) INFORMATION FOR SEQ ID NO:85:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:85:

GGCGCTTCAG GGAGTGCAT                                                     19

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:86:

CGGCGCTTCA GGGAGTGCAT                                                    20

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:87:

CGGCGCTTCA GGGAGTGCAT                                                    20

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:88:

CCCGGCGCTT CAGGGAGTGC AT                                                 22

(2) INFORMATION FOR SEQ ID NO:89:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:89:

GCCCGGCGCT TCAGGGAGTG CAT                                                23

(2) INFORMATION FOR SEQ ID NO:90:

(i) SEQUENCE CHARACTERISTICS:
```

```
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:90:

AAGAACACAG CTGGGCTCAG GGC                                                    23
```

IMMUNOGLOBULIN TRANS-SPLICED TRANSCRIPTS AND USES THEREOF

The present application claims benefit of U.S. Provisional Application No: 60/023,579, filed Aug. 19, 1996.

The government owns certain rights in the present invention pursuant to grant number AI-15251 from the U.S. Public Health Service and grant number AI-34567 from the National Institutes of Allergy and Infectious Diseases, and Environmental Health Science.

FIELD OF THE INVENTION

The present invention relates generally to the fields of immunology and allergy. More particularly, it concerns compositions and methods useful for stimulating or inhibiting synthesis of a particular human immunoglobulin isotype. Methods of treatment for disorders mediated by IgM, IgG, IgA or IgE are provided and, in particular, inhibition of IgE synthesis is helpful for patients suffering from allergy disorders.

BACKGROUND OF THE INVENTION

Immunoglobulin (Ig) refers to the immunity-conferring portion of the globulin proteins of serum. The terms antibody and immunoglobulin are frequently used interchangeably. Ig's are secreted by differentiated B cells termed plasma cells; the Ig monomers are made up of two identical heavy chains (H) and two identical light chains (L). Each light chain is attached to a heavy chain by disulfide bonds, and the heavy chains are also attached to each other by one or more disulfide bonds. Each chain is a sequence of amino acids folded into a series of globular domains, the four chains together form a "Y"-shaped structure.

Each antibody or immunoglobulin has specific binding affinity for the foreign material or antigen that stimulated its synthesis. The globular domains at the branched ends of the "Y"-shaped molecule, termed variable domains (V), bind antigen. The variable domains together form a binding cavity that is geometrically and chemically complementary to a single type of antigen, allowing a fit of the cavity with the antigen. These domains are referred to as "variable" because the amino acid sequence of these domains varies according to antibody specificity. For example, an antibody binding the protein insulin will have a different amino acid sequence at the "variable" domains (binding sites) compared to an antibody that binds the protein keratin.

The globular domains of the "stem" portion of the "Y"-shaped molecule are called constant (C) domains. The amino acid sequences of these constant domains, for the most part, do not vary. However, sufficient differences exist for five major classes of Ig's to be identified in serum, each class containing a specific heavy chain. These "constant" portions of an immunoglobulin molecule determine biological activity such as the ability of immunoglobulins to bind to cells, to fix complement, and to traverse the placenta, for example. These classes of immunoglobulins and their heavy chains are as follows:

IgG (γ chain): the principal immunoglobulin in serum, the main antibody raised in response to an antigen, this antibody crosses the placenta;

IgE (ε chain): this Ig binds tightly to mast cells and basophils, and when additionally bound to antigen, causes release of histamine and other mediators of immediate hypersensitivity; plays a primary role in allergic reactions, hay fever, asthma, and anaphylaxis; this role does not appear to serve any useful purpose for a human; may serve a protective role against parasites;

IgA (α chain): the Ig present in external secretions, such as saliva, tears, mucous, and colostrum;

IgM (μ chain): the Ig first induced in response to an antigen, it has lower affinity than antibodies produced later and is pentameric; and IgD (δ chain): this Ig is found in relatively high concentrations in umbilical cord blood, may be an early cell receptor for antigen, and is the main lymphocyte cell surface molecule.

An IgG, IgE, IgA, IgM, and IgD antibody may have the same variable regions, i.e., the same antigen binding cavities, even though they differ in the constant region of their heavy chains.

These classes of immunoglobulins are also described as being isotypes of immunoglobulins. Further, immunoglobulin isotypes have subclasses, for example, IgG has four subclasses of heavy chains, γ1, γ2, γ3, and γ4, each different in structure and biological properties; IgE has one heavy chain, ε; IgA has two subclasses of heavy chain, α1 and α2; IgM has one heavy chain μ; and IgD has one heavy chain δ. A light chain of an immunoglobulin is either a kappa or lambda chain.

During development, stem cells formed in a yolk sac, liver, or bone marrow migrate to lymph nodes and the spleen where individual cell lines undergo clonal development independent of antigen stimulation. Most cells initially produce IgM, and later switch to IgG, IgE, or IgA production. Once B cells are released into the circulation and reach peripheral lymphoid tissues, they are capable, if stimulated by antigen, of differentiating into plasma cells that produce antibody specific for the antigen encountered.

Antibody diversity is a consequence of somatic recombination in germline DNA-encoding immunoglobulin regions, and RNA splicing of transcripts. Germline DNA carries instructions for nine constant region genes encoding the heavy chain isotype subclasses in linear order; μ, δ, γ3, γ1, α1, γ2, γ4, ε, and α2. Isotype switching, DNA deletion, transcription and splicing have been the proposed mechanisms for producing the final messenger RNA that is translated by ribosomes to form a heavy chain immunoglobulin protein.

Ig isotype switching is preceded by germline transcription from the heavy chain locus that will subsequently undergo switch recombination. Germline transcription initiates at a non-coding exon (termed I exon) located upstream of a switch region; I exons generally display multiple stop codons in all reading frames and cannot code peptides of significant length (2–7). Germline transcription has been thought to participate in class switching by altering chromosome structure to provide recombinase accessibility (5–7). Although spliced and processed germline transcripts have been shown to be necessary (8), the exact role of processed germline transcripts in isotype switching has remained heretofore unknown.

Shimizu et al. reportedly indicated that mice transgenic with a rearranged membrane human VDJ-Cμ gene produced chimeric Ig mRNAs with human VDJ correctly spliced to endogenous mouse Cγ1 and Cε through a trans-splicing mechanism (14–17). Although trans-splicing was not demonstrated, a mouse hybrid germline transcript of Iμ-Cγ2b was reportedly provided by Li et al. (43).

Trans-splicing has been well delineated in trypanosomes, where many mRNAs trans-splice using an identical 5'35 nucleotide leader (termed splicing leader) (4648). A similar splicing leader (22 nucleotides) has been identified in nemotodes (49). However, both of these organisms employ a unique catalytic intron for trans-splicing not known to be present in humans.

An IgE-mediated allergy reaction results from the binding of an allergen (such as found in pollen, dander or dust) to IgE that is bound to the surface of basophils and mast cells; such binding causes crosslinking of underlying receptors, and the subsequent release of pharmacological mediators, such as histamine, causes the well known symptoms of allergy. Common allergies are estimated to affect routinely 10 to 20% of the population.

Treatment of allergy is complex and variable, but can be divided into three main approaches. Environmental controls are designed to eliminate or at least minimize exposure to the allergen. Symptomatic drug therapy is required in the control of most common allergies. The many drugs used for this purpose include the antihistamines and systemic and topical corticosteroids and sympathomimetics. Immunotherapy of allergy is accomplished by administration of gradually increasing doses of allergen over a period of months or years with the hope that the patient will develop increasing tolerance to the allergen. The precise mechanism of immunotherapy still is unknown, however, clinical improvement in some patients correlates well with the level of IgG-blocking antibodies, which presumably act by binding the allergen and preventing its interaction with mast cell-bound IgE. Immunotherapy isn't consistently effective for all sufferers of allergic symptoms; further, the immunotherapy regimen can be costly and require significant discipline on the part of the patient for success. Risks include local reactions at the injection site, and the possibility of serious generalized allergic reactions. Treatment failures may result from improper selection of allergens, development of new sensitivities, improper use of environmental controls and problems associated with the allergenic extracts. Alternative treatment includes steroid injections that generally suppress the whole immune system, a strategy that, by definition, puts the patient at risk.

Prior to the present invention, there have been no compositions or methods available for direct stimulation or inhibition of synthesis by modulating switching at a nucleic acid level of a particular human immunoglobulin isotype. Therefore, the present inventors have searched for improvements in this art and provide the compositions and methods described herein.

SUMMARY OF THE INVENTION

The present invention results from the inventors' discovery that trans-spliced ribonucleic acid transcripts comprising at least a portion transcribed from an I region of genomic immunoglobulin heavy chain DNA trans-spliced to at least a portion transcribed from a C region of genomic immunoglobulin heavy chain DNA are bridging templates for recombination of genomic DNA, which recombination results in immunoglobulin isotype switching.

An embodiment of the present invention is a purified nucleic acid molecule comprising a first nucleotide sequence of at least about 8 nucleotides capable of annealing to a human genomic immunoglobulin heavy chain I region of a first locus selected from the group of loci consisting of $\mu$, $\epsilon$, $\alpha$, and $\gamma$, covalently bonded in a 5' to 3' orientation to a second nucleotide sequence of at least about 8 nucleotides capable of annealing to a human genomic immunoglobulin heavy chain C region of a second locus selected from the group of loci consisting of $\mu$, $\epsilon$, $\alpha$, and $\gamma$. In this embodiment, the first locus is different from the second locus, and when the purified nucleic acid molecule is annealed to human genomic immunoglobulin DNA, a first genomic immunoglobulin heavy chain locus switch region is brought into sufficient physical proximity to a second genomic immunoglobulin heavy chain locus switch region to allow recombination between the first switch region and the second switch region.

As used herein, the term "a purified nucleic acid molecule" refers to a DNA or an RNA molecule that is isolated away from, or purified free from total human genomic nucleic acid, i.e., total genomic DNA or total genomic RNA. One skilled in this art, in light of this disclosure, will realize that the nucleotide "T" indicating thymine in sequences of nucleic acids as presented herein may be substituted with a "U" indicating uracil, since the bridging templates and antisense molecules of the present invention may be either RNA or DNA.

"A nucleotide sequence of at least about 8 nucleotides" means that this portion of the claimed nucleic acid molecule is at least about 8 nucleotides long, the portion may contain at least 6, 7, 8, or 9 nucleotides as one of skill in the art realizes that the hybridization bond between purine residues is stronger than that between pyrimidine residues, and therefore, a sequence rich in purines may not need to be as long as a sequence rich in pyrimidines.

"Capable of annealing" means that the cited portion of the nucleic acid molecule has sufficient sequence complementarity to a human genomic immunoglobulin heavy chain DNA nucleotide sequence so as to form hydrogen bonds with that DNA.

"A human genomic immunoglobulin I region of a first locus selected from the group of loci consisting of $\mu$, $\epsilon$, $\alpha$, and $\gamma$," means an I region from a human I$\mu$, I$\epsilon$, I$\alpha$1, I$\alpha$2, I$\gamma$1, I$\gamma$2, I$\gamma$3, or I$\gamma$4 immunoglobulin DNA. An "I" region is a region of immunoglobulin heavy chain DNA that is a noncoding exon positioned 5' of a switch region and is deleted in a switched Ig gene except for $\mu$. The I region of $\mu$ shares sequences with the enhancer region and becomes part of the switched Ig genes. Examples of I regions are shown in FIG. 1. "A locus" as used herein means a unit of genomic immunoglobulin heavy chain DNA that includes an I region, a switch region, and a constant region of one immunoglobulin isotype. For example, I$\mu$, S$\mu$, and C$\mu$ form the $\mu$ locus.

"A human genomic immunoglobulin heavy chain C region of a second locus selected from the group of loci consisting of $\mu$, $\epsilon$, $\alpha$, and $\gamma$," means a C region from a human C$\mu$, C$\gamma$, C$\alpha$1, C$\alpha$2, C$\gamma$1, C$\gamma$2, C$\gamma$3, or C$\gamma$4 immunoglobulin DNA. A "C" region, as used herein, is a constant chain region of immunoglobulin DNA that is transcriptionally active and in germ line configuration.

"The first locus is different from the second locus" means that the I portion of a nucleic acid molecule may not be from the same locus as the C portion. For example, an I portion cannot be from a $\mu$ locus if the C portion is from a $\mu$ locus.

"When the purified nucleic acid molecule is annealed to human genomic immunoglobulin DNA, a first genomic immunoglobulin locus switch region is brought into sufficient physical proximity to a second genomic immunoglobulin locus switch region to allow recombination between the first switch region and the second switch region" means that the nucleic acid molecule has the property that when annealed or hybridized to human genomic immunoglobulin heavy chain DNA, the molecule acts as a bridging template to bring the said switch regions in sufficient proximity for recombination to occur. Recombination may be carried out by the enzyme, recombinase, for example. Immunoglobulin switch regions and the catalytic action of the enzyme recombinase are known in the art in light of this disclosure.

As used herein, "isotype switching" means a change in phenotype of an antibody-producing cell. For example, B cells initially produce primarily IgM antibody, a phenotypic change to the production of IgE, IgG, or IgA is an isotype switch. Isotype switching, as used herein, includes two steps; the first step is the provision of trans-spliced transcripts to act as bridging templates for conforming genomic immunoglobulin DNA, and the second step is switch recombination that results in the production of switch circles and rearrangement of genomic immunoglobulin DNA to allow production of a different antibody.

Switch recombination to isotype IgE, for example, may be catalyzed by recombinase when a trans-spliced transcript, such as Iε-Cμ or Iμ-Cε, acts as a bridging template to bring an ε switch region in sufficient physical proximity to a μ switch region. Trans-spliced transcripts for recombination to particular isotypes are provided in Table 1.

TABLE 1

Trans-spliced Transcripts as Templates for
Isotype Switching from IgM to Isotype:

| IgE | IgG | IgA |
|---|---|---|
| Iε-Cμ | Iγ-Cμ | Iα-Cμ |
| Iμ-Cε | Iμ-Cγ | Iμ-Cα |

The trans-spliced transcripts cited in Table 1 are provided by the present invention as effective in switching the isotype of a B cell, resulting in change of phenotype of the cell.

Further trans-spliced transcripts of the present invention, such as Iε-Cα, Iε-Cγ, Iγ-Cε, Iγ-Cα, Iα-Cε, Iα-Cγ are not expected to affect a present phenotype of a cell. However, these transcripts can be used to effect a targeted deletion of heavy chain loci and therefore prevent switching to a deleted locus. For example, the germline configuration of heavy chain loci is μ, δ, γ3, γ1, γ2, γ4, ε, and α2; the transcript Iγ4-Cα2 would force a cell to delete the γ4 and ε constant regions, therefore, that cell would be unable to switch to an IgE isotype. This process of deletion is also referred to as "sterile" switching. One of skill in the art, in light of these teachings, would realize that other constant regions of the germline DNA could be deleted to prevent switching to the deleted isotype.

An assay for testing whether an oligonucleotide or a nucleic acid molecule is effective for acting as a bridging template for switch recombination is the detection of recombined switch region DNA. The assay uses the polymerase chain reaction as set forth in the examples using primer sets as follows: for detecting switch region DNA recombined from μ to γ, M2 and SG1 (Table 5); for detecting switch region DNA recombined from μ to ε, M2 and E8 (Table 5); and for detecting switch region DNA recombined from μ to α, M2 (Table 5) and Pα AAGAACACAGCTGGGCT-CAGGGC (Islam et al., J. Immunol. 1994, 152:1442), SEQ ID NO. 90. One of skill in the art in light of these teachings would be able to assemble primer set combinations to assay for "sterile" switching using the primer position information set forth in FIG. 1 and the primer sequence information provided in Table 5.

A bridging template nucleic acid molecule of the present invention has a 5' sequence from a 3' end of an I region of a first locus, and has a 3' sequence from a 5' end of a C exon region of a second locus. In further embodiments of the nucleic acid molecules of the present invention: the first locus is μ and the second locus is E, or the first locus is ε and the second locus is μ, for switching to ε; the first locus is μ and the second locus is γ, or the first locus is γ and the second locus is μ, for switching to γ; or the first locus is μ and the second locus is α, or the first locus is α and the second locus is μ, for switching to α.

In particular embodiments of the bridging templates of the present invention, the molecules may have nucleotide sequences set forth as SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 50, SEQ ID NO. 53, SEQ ID NO. 57, SEQ ID NO. 59, SEQ ID NO. 61, SEQ ID NO. 63, SEQ ID NO. 65, or SEQ ID NO. 68.

A bridging template may have a length that further includes any part of or the complete length of an I or C region. An embodiment of a bridging template nucleic acid molecule is where the first locus is E and the first nucleotide sequence is an about 10, 15, 20, 25, 30, 35, 40, 45, 50, 55, 60, 65, 70, 75, 80, 85, 90, 95, 100, 105, 110, 115, 120, 125, 130, or 135 nucleotide sequence from SEQ ID NO. 70. A further embodiment is where the first locus is μ and the first nucleotide sequence is an about 10, 20, 30, 40, 50, 75, 100, 150, 200, 250, 300, 350, 400, 450, 500, 550, 600, or 644 nucleotide sequence from SEQ ID NO. 71. Another embodiment is where the second locus is ε and the second nucleotide sequence is an about 10, 20, 30, 40, 50, 75, 100, 150, 200, 300, 400, 500, 600, 700, 800, 900, 1000, 1100, 1200 or 1284 nucleotide sequence from SEQ ID NO. 72. Another embodiment is where the second locus is μ and the second nucleotide sequence is an about 10, 20, 30, 40, 50, 75, 100, 150, 200, 250, 300, 350, 400, or 429 nucleotide sequence from SEQ ID NO. 73.

The present invention also includes nucleic acid molecules that are complementary to the nucleic acid molecules described herein. Complementary nucleic acid molecules obey Watson-Crick base pairing rules and the single-stranded nucleotide sequence of a complementary molecule is typically also written in a 5' to 3' direction. Complementary nucleic acid molecules are sometimes referred to as antisense molecules, meaning that they are complementary to the sense strand of DNA, they are complementary to messenger RNA (a sense strand), and they have identical sequence to the antisense strand of DNA. When annealed to messenger RNA, antisense molecules may inhibit the function of the messenger RNA; and when annealed to duplex DNA, the molecule is termed a triplex and the antisense molecule may inhibit the function of the duplex DNA.

An embodiment of the invention is a purified antisense nucleic acid molecule comprising a first nucleotide sequence of at least about 8 nucleotides having sequence identity with an antisense strand of a human genomic immunoglobulin heavy chain C region of a first locus selected from the group of loci consisting of μ, ε, γ, and α, covalently bonded in a 5' to 3' orientation to a second nucleotide sequence of at least about 8 nucleotides having sequence identity with an antisense strand of a human genomic immunoglobulin heavy chain I region of a second locus selected from the group of loci consisting of μ, ε, γ, and α. The first locus is different from the second locus, and when the purified antisense nucleic acid molecule is annealed to human trans-spliced immunoglobulin heavy chain chimeric ribonucleic acid transcript involved in switch recombination, a hybrid duplex is formed, thereby inhibiting activity of the trans-spliced transcript as a template for recombination and inhibiting isotype switching.

Antisense nucleic acid molecules are useful for inhibiting or blocking isotype switching or channeling isotype switching away from an undesired isotype, such as away from production of IgE, for example. Sense bridging templates may be provided at the same time to encourage switching towards a more benign isotype, towards the production of IgG or IgA, for example.

A particular embodiment of an antisense molecule is where the first locus is μ and the second locus is ε, or where the first locus is ε and the second locus is μ. A further particular embodiment is where the antisense molecule has a nucleotide sequence set forth as SEQ ID NO. 2, SEQ ID NO. 4, SEQ ID NO. 6, SEQ ID NO. 8, SEQ ID NO. 10, SEQ ID NO. 12, SEQ ID NO. 14, or SEQ ID NO. 16.

Table 2 lists the identity of sequences of the present disclosure having sequence identifiers.

TABLE 2

Identification of Sequences Having Sequence Identifiers

| SEQ ID NO: | IDENTITY |
|---|---|
| 1 | nucleotide sequence of Iμ-Cε "core" bridging nucleic acid molecule |
| 2 | antisense sequence of SEQ ID NO. 1 |
| 3 | nucleotide sequence of Iε-Cμ "core" bridging nucleic acid molecule |
| 4 | antisense sequence of SEQ ID NO. 3 |
| 5 | nucleotide sequence of Iγ4-Cμ "core" bridging nucleic acid molecule |
| 6 | antisense sequence of SEQ ID NO. 5 |
| 7 | nucleotide sequence of Iμ-Cγ4 "core" bridging nucleic acid molecule |
| 8 | antisense sequence of SEQ ID NO. 7 |
| 9 | nucleotide sequence of Iε-Cγ4 "core" bridging nucleic acid molecule |
| 10 | antisense sequence of SEQ ID NO. 9 |
| 11 | nucleotide sequence of a first Iγ4-C" "core" bridging nucleic acid molecule using a first splicing site |
| 12 | antisense sequence of SEQ ID NO. 11 |
| 13 | nucleotide sequence of a second Iγ4-Cε "core" bridging nucleic acid molecule using a second splicing site |
| 14 | antisense sequence of SEQ ID NO. 13 |
| 15 | nucleotide sequence of Iγ4-Cα1 "core" bridging nucleic acid molecule |
| 16 | antisense sequence of SEQ ID NO. 15 |
| 17–48 | nucleotide sequence of primers of Table 5 |
| 49 | nucleotide sequence of gIμ/Eμ junction |
| 50 | nucleotide sequence of Iμ-Cε bridge, clone P12-15 |
| 51 | nucleotide sequence of gCHε |
| 52 | nucleotide sequence of gIε-Sε junction |
| 53 | nucleotide sequence of Iε-Cμ bridge, clone P31-18 |
| 54 | nucleotide sequence of gCHμ |
| 55 | nucleotide sequence of gCHμ |
| 56 | nucleotide sequence of gIγ4-Sγ4 junction |
| 57 | nucleotide sequence of Iγ4-Cμ bridge, clone P165-2 |
| 58 | nucleotide sequence of gCHμ |
| 59 | nucleotide sequence of Iμ-Cγ4 bridge, clone P26-2 |
| 60 | nucleotide sequence of gCHγ4 |
| 61 | nucleotide sequence of Iε-Cγ4 bridge, clone P112-1 |
| 62 | nucleotide sequence of IE-Cγ4 bridge, clone P112-1 |
| 63 | nucleotide sequence of Iγ4-Cα 1 bridge, clone P131-8 |
| 64 | nucleotide sequence of gCHα 1 |
| 65 | nucleotide sequence of Iγ4-Cε bridge at a first splice site, clone P88-1 |
| 66 | nucleotide sequence of gCHε |
| 67 | nucleotide sequence of gIγ4-Sγ4 junction |
| 68 | nucleotide sequence of Iγ4-Cε bridge at a second splice site, clone P88-2 |
| 69 | nucleotide sequence of gCHε |
| 70 | nucleotide sequence of human Iε exon from Gauchat (33) |
| 71 | nucleotide sequence of human Iμ exon from Neale (35) |
| 72 | nucleotide sequence of human Cε exon from Max (40) |
| 73 | nucleotide sequence of human Cμ exon from Neale (35) |
| 74 | probe PG (FIG. 1) corresponding to the γ4 CH1 region |
| 75 | probe PE (FIG. 1) corresponding to an εCH1 region |
| 76–89 | exemplary embodiments of Iε-Cμ bridging template molecule |
| 90 | nucleotide sequence of one primer for detecting switch region DNA recombined to α; AAGAACACAGCTGGGCTCAGGGC |

A further aspect of the present invention is a purified human triplex nucleic acid molecule comprising a duplex DNA molecule annealed to a bridging template nucleic acid molecule of the present invention. The bridging template molecule may be DNA or RNA, and is preferably RNA. Another embodiment of the invention is a purified human duplex nucleic acid molecule comprising an antisense DNA molecule of a bridging template molecule of the present invention annealed to a trans-spliced messenger RNA molecule. The antisense DNA molecule annealed to the mRNA molecule would inhibit template binding activity of the trans-spliced mRNA molecule.

Further embodiments of the present invention include a recombinant vector comprising a purified nucleic acid molecule as herein described for a bridging template or for an antisense molecule. Preferably, the recombinant vector is an expression vector comprising a promoter operatively linked to said nucleic acid molecule. Exemplary vectors are known to those of skill in the art in light of this disclosure and include, but are not limited to, a herpes virus, cytomegalovirus, adenoviral, adeno-associated viral, retroviral, or plasmid vector. In particular, the vector is a cytomegalovirus vector. By way of example, the cytomegalovirus vector may be PBK-CMV.

A recombinant host cell comprising a recombinant vector having a purified nucleic acid molecule as described herein is a further aspect of the invention. Preferably, a recombinant host cell is an immunoglobulin-producing cell, such as a B cell. In some embodiments, the B cell is a primary B cell, such as a human primary B cell. The recombinant host cells of the invention in some embodiments comprise host cells such as E. coli, yeast cells, or baculovirus carrying cells that include the recombinant vector or nucleic acid described herein. In other embodiments, the recombinant host cell is a human EBV transformed cell line GM1500 that includes the recombinant vector or nucleic acid of the present invention.

Method for reducing production of IgE, reducing isotype switching to IgE, or treating allergy in a human subject are further aspects of the present invention. In some embodiments, these methods comprise administering to the subject a preparation comprising a purified antisense nucleic acid molecule as herein described. For example, the purified antisense nucleic acid molecule may be defined as comprising a first locus μ and a second locus E, or a first locus ε and a second locus μ. Preparations that include such purified antisense nucleic acid may then be provided to the patient in an amount sufficient to inhibit template binding activity of an in vivo trans-spliced transcript involved in switch recombination to IgE, and thereby reducing production of IgE compared to a normal level. Reduction of IgE compared to a normal level provides at least one parameter that may be used to establish that a therapeutically effective treatment of the allergy has occurred.

In some embodiments, the purified antisense nucleic acid molecule has a nucleotide sequence comprising a sequence essentially as set forth at SEQ ID NO. 2 or SEQ ID NO. 4. Such an agent may be administered to a patient at risk of an allergic reaction, so as to provide a method of preventing or at least reducing an allergic response, or may be administered to an animal suffering from an existing allergic reaction so as to provide a method of treating the allergic reaction.

A method for enhancing production of IgE in a human subject is a further embodiment of the present invention. In some embodiments, the method comprises administering to the subject a purified nucleic acid molecule bridging template as herein described, where the first locus is μ and the second locus is ε, or where the first locus is ε and the second locus is μ, in an amount sufficient to enhance production of IgE compared to a normal level in the subject. In a preferred embodiment, the nucleic acid molecule has a nucleotide sequence comprising a sequence essentially as set forth at SEQ ID NO. 1 or SEQ ID NO. 3.

In yet another aspect, the invention provides a method for enhancing production of IgG in a human subject. In some embodiments, the method comprises administering to the subject a purified nucleic acid molecule as herein described, where the first locus is μ and the second locus is γ, or where the first locus is γ and the second locus is μ, in an amount sufficient to enhance production of IgG compared to a normal level in the subject. Preferably, the purified nucleic acid molecule has a nucleotide sequence comprising a sequence essentially as set forth at SEQ ID NO. 5 or SEQ ID NO. 7. This method or equivalents of this method may be used, for example, for enhancing production of IgG in an immune-depleted state, such as in common variable immunodeficiency, for example.

In another aspect, the invention provides a method for enhancing production of IgA in a human subject. In one embodiment, the method comprises administering to the subject a purified nucleic acid molecule as herein described, where the first locus is μ and the second locus is α, or where the first locus is α and the second locus is μ, in an amount sufficient to enhance production of IgA compared to pre-treatment IgA levels in the subject. In some embodiments, the purified nucleic acid molecule has a nucleotide sequence comprising a sequence essentially as set forth at SEQ ID NO. 15. Enhancing production of IgA may be desirable in persons with Ig A deficiency. This occurs in approximately 1:2000 people and is associated with frequent and severe respiratory infections.

For these methods of inhibition of isotype switching to IgE or methods of enhancement of isotype switching to IgE, IgG, or IgA levels, any change resulting in less than, or greater than, normal levels, respectively, or what would be normal if intervention was not pursued, is considered inhibition or enhancement. As used herein, a normal level may be defined as the level of the particular immunoglobin in the patient during a non-diseased state, i.e., such as in the absence of an allergic reaction, or a normal level as determined from a mean average from a population of human adults. Normal levels of the various immunoglobulins in an adult human population are as follows: An adult average level of IgE in serum is about 0.0024 to about 0.024 mg/100 ml; of IgG is about 600 to about 1500 mg/100 ml; and of IgA is about 75 to about 300 mg/100 ml.

Another aspect of the present invention is a method of detecting a trans-spliced transcript in a human B cell comprising the steps of obtaining cDNA from stimulated human B cells, amplifying the cDNA to produce an amplified product, and identifying the amplified product as a trans-spliced transcript. Methods for identification of an amplified product as a trans-spliced transcript are taught in Examples 1 and 2, and include primer sequences and fragment sizes from agarose gels. B cells can be stimulated in vitro using a cytokine stimulating molecule such as, but not limited to, IL-4 or IL-10, and an anti-CD40 antibody, for example. A stimulatory agent is not needed in vivo since the human body would provide such factors.

Following long-standing patent law convention, the terms "a" and "an" mean "one or more" when used in this application, including the claims. The various nucleic acid sequences, fragments, and constructs described herein have a number of utilities, including uses as reagents in the detection of trans-spliced transcripts, as well nucleic markers, and are uses readily recognizable by those of ordinary skill in the art given the present disclosure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
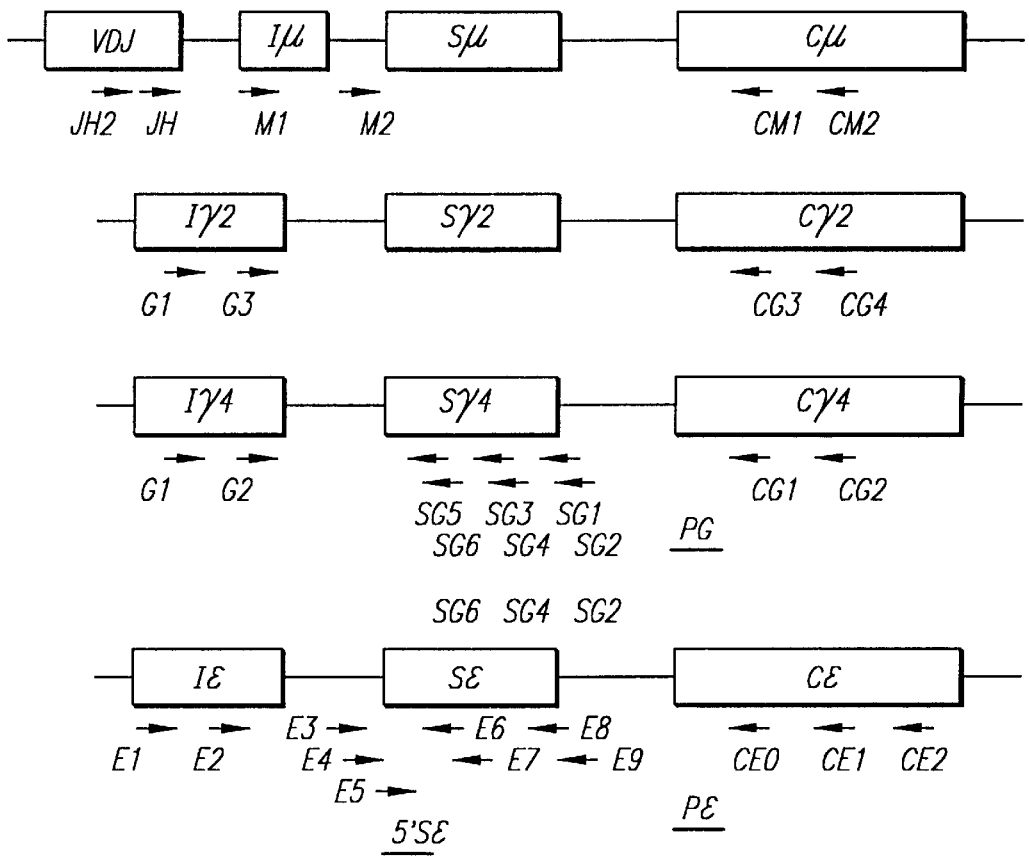
FIG. 1. provides a diagram of human IgH chain regions showing the germline μ, germline γ2, γ4 and ε loci. The relative position and direction of the PCR primers employed are shown with arrows. S represents the switch region, I represents the I exon of the germline transcripts and C represents the constant region exons. PG, 5'Sε and PE are probes for Southern blots.

The present invention provides nucleic acid molecules that include, among others, bridging templates or chimeric molecules comprising a constant region sequence of a downstream transcriptionally active but non-switched immunoglobulin nucleic acid sequence attached directly or indirectly to a nucleic acid sequence from an I region of any transcriptionally active IgH gene. The chimeric molecule may thus be described as having a constant region and an I region from different immunoglobulin heavy chain loci. Chimeric mRNAs are produced in vivo by trans-splicing between two different pre-mRNAs. The present invention provides chimeric mRNAs that act as bridging templates, and as such function in conforming and/or patterning genomic DNA so as to direct the specificity of isotype switching. By manipulating the production or activity as templates of these mRNAs, switching to specific immunoglobulin isotypes is enhanced. It is envisioned that the induction of an allergic response may be reduced or prevented both systemically and locally at the airway mucosa using compositions and methods of the present invention. It is also envisioned that isotype stabilization may be blocked, so that should cells switch to an isotype such as IgE, they do not become stable at that point and then will subsequently switch to another potentially less "harmful" isotype such as IgA.

Immune Effector Applications

Allergy can be divided into four types on the basis of the immune effectors, mediators and cells involved in the reaction as provided in Table 3.

TABLE 3

Mechanisms and Manifestations of Allergy[a]

|  | Type I | Type II | Type III | Type IV |
|---|---|---|---|---|
| Name(s) | Immediate Reagin-mediated | Cytotoxic | Immune complex Arthus type | Delayed: Cellular-mediated Tuberculin-Type |
| Immune effectors | IgE | IgG; IgM | IgG (IgM) | Effector T cells |
| Cells involved in inflammation | Mast Cells Basophils | Macrophages (cell-mediated lysis) or | Neutrophils | Macrophages Lymphocytes |
| Mediators | Histamine Leukotrienes | Complement (C'-mediated lysis) | Lysosomal enzymes | Lymphokines |
| Time of onset in sensitized individuals | 0–30 min | Immediate but may not be apparent for some time | 2–24 hr | 6–24 hr |
| Manifestations | Rhinitis Urticaria Angioedema Asthma Anaphylaxis | Hemolytic anemia Neutropenia Thrombocytopenia | Serum sickness Vasculitis Glomerulonephritis Extrinsic alveolitis | Contact dermatitis Allergy of many infections |

[a]Based on classification of Coombs and Gell in: Gell PGH, Coombs RRA, Lachmann PJ, eds: Clinical Aspects of Immunology, Blackwell, London, 1975. From "Allergenic Extracts," Shough, HR in: Gennaro, AR, ed: Remington: The Science and Practice of Pharmacy, Mack Pub. Co., Easton, PA, 1995.

It is contemplated that compositions provided by the present invention may be used to alleviate any manifestation where an immunoglobulin molecule is an immune effector, in particular, those manifestations cited in Table 3. Most of the common allergies to environmental allergens involve the Type I immediate reactions. IgE is the immune effector for this type of allergy, whereas IgG, IgM and/or IgA are immune effectors for Type II and Type III allergic reactions, reactions that are prominent in autoimmune and alloimmune diseases. Compositions and methods of the present invention are contemplated as particularly useful for "steering" isotype switching away from a particular isotype that may be involved in the undesired manifestations and, at the same time, other compositions and methods of the present invention may be used to encourage switching to a particularly benign isotype. Other conditions that could be treated using compositions and methods of the present invention include IgA nephropathy or Henlock Schonlien purpura where an IgA antibody is pathogenic, or the condition of IgA deficiency where failure to make IgA leads to recurrent infection.

"IgG" as used herein means any of the subclasses of IgG: Ig1, Ig2, Ig3, or Ig4. "IgA" as used herein means any of the subclasses of IgA: Iα or Iα2.

Bridging Template Nucleic Acid Embodiments

As an example of a bridging template, or a trans-spliced transcript as is also used herein, a sequence at the splice junction of an Iε-Cμ trans-spliced transcript from clone P31-18 is provided below as SEQ ID NO:53; the portion in italic font is from Iε, and the portion in normal font is from Cμ:

The junction of the italicized nucleotides and those in normal font represents a splice junction as determined by the present inventors. In some embodiments, nucleic acid molecules having at least about 8 nucleotides from the Iε portion immediately 5' of the splice junction covalently bonded to at least about 8 nucleotides from the Cμ portion immediately 3' of the splice junction, and functional equivalents thereof, are useful for enhancing recombination to the IgE isotype.

A nucleic acid molecule having at least about 8 nucleotides from each side of the splice junction of the sequence of SEQ ID NO:53 is CGCTTCAGGGAGTGCA, (SEQ ID NO: 3), termed a "core" bridging template or "core" nucleic acid molecule of the present invention. One of skill in this art would realize in light of the present disclosure that any number of nucleotides 5' or 3' to this sequence found in SEQ ID NO: 53 may be included in the same order as indicated in SEQ ID NO: 53 above to provide further embodiments of nucleic acid molecules useful for the same purpose. For example, sequences at the 3' Cμ end of a bridging template can include any number of nucleotides from the sequence of Cμ as follows:

```
         Iε                                    Cμ
5' AGGCACCAAATGGACAGCCCGGCGCTTCAGGGAGTGCATCCAGCCCCAACCCTTTTCCCC 3' SEQ ID NO: 53
```

```
              Iε                                      Cμ

5'  AGGCACCAAATGGACAGCCCGGCGCTTCAGGGAGTGCATCCAGCCCCAACCCTTTTCCCC    3'  SEQ ID NO: 53

5'                         CGCTTCAGGGAGTGCAT                        3'  SEQ ID NO: 76

5'                         CGCTTCAGGGAGTGCATC                       3'  SEQ ID NO: 77

5'                         CGCTTCAGGGAGTGCATCC                      3'  SEQ ID NO: 78

5'                         CGCTTCAGGGAGTGCATCCA                     3'  SEQ ID NO: 79

5'                         CGCTTCAGGGAGTGCATCCAG                    3'  SEQ ID NO: 80

5'                         CGCTTCAGGGAGTGCATCCAGC                   3'  SEQ ID NO: 81

5'                         CGCTTCAGGGAGTGCATCCAGCC                  3'  SEQ ID NO: 82

5'                         CGCTTCAGGGAGTGCATCCAGCCC (etc.)          3'  SEQ ID NO: 83
```

The complete Cμ exon (SEQ ID NO. 73) is the upper limit for the length of the C nucleotide portion of a bridging template for Cμ. Sequences toward the 5' Iε end of a bridging template can include any number of nucleotides from the sequence of Iε as follows:

```
              Iε                                      Cμ

5'  AGGCACCAAATGGACAGCCCGGCGCTTCAGGGAGTGCATCCAGCCCCAACCCTTTTCCCC    3'  SEQ ID NO: 53

5'                         GCGCTTCAGGGAGTGCAT                       3'  SEQ ID NO: 84

5'                         GGCGCTTCAGGGAGTGCAT                      3'  SEQ ID NO: 85

5'                         CGGCGCTTCAGGGAGTGCAT                     3'  SEQ ID NO: 86

5'                         CCGGCGCTTCAGGGAGTGCAT                    3'  SEQ ID NO: 87

5'                         CCCGGCGCTTCAGGGAGTGCAT                   3'  SEQ ID NO: 88

5'          (etc.) GCCCGGCGCTTCAGGGAGTGCAT                          3'  SEQ ID NO: 89
```

The complete Iε exon (SEQ ID NO. 70) is the upper limit for the length of the I nucleotide portion of a bridging template for Iε. Further, any combination of nucleotides extending in either the 5' or 3' direction of a "core" sequence is contemplated as an embodiment of the present invention. One skilled in the art in light of this disclosure would be able to construct the rest of the molecules useful as bridging templates for this I-C combination, as well as the other I-C combinations provided herein. Any combination of the above sequences would also provide a nucleic acid molecule that would act as a template for recombination as long as it has the core of about 16 nucleotides that bridge the splice junction. The upper limit for the 5' end of the Iε portion is the entire Iε exon which is about 130 nucleotides, although a number of transcription initiation sites exist. The sequence of the Iε exon and positions of various transcription initiation sites are provided as SEQ ID NO. 70 and in Gauchat et al., (1990, *J. Exp. Med.* 172:463), which reference is incorporated by reference herein for the stated purpose. The upper 3' limit of the Cμ portion is the entire Cμ exon of about 1.2 kb, the sequence of which is presented as SEQ ID NO. 73 and in Neale and Kitchingman (1991, *Nucl. Acids Res.* 19:2427), which reference is incorporated by reference herein for the purpose stated.

Similarly, the upper limit of the 5' end of an Iμ portion is the entire Iμ exon of about 640 nucleotides, the sequence of which is provided as SEQ ID NO. 71 and in Neale and Kitchingman (1991, *Nucl. Acids Res.* 19:2427), which reference is incorporated by reference herein for the purpose stated. The upper limit of the 3' end of a Cε portion is the entire exon of about 1.2 kb, the sequence is provided as SEQ ID NO. 72 and in Max et al., (1982, *Cell* 29:691), incorporated herein by reference for the purpose stated. The upper limit of the 3' end of a Cγ portion is the entire exon of about 900 bp, the Iγ exon is also the outer limit of the 5' end of an Iγ portion of about 440 bp for Iγ1 (31).

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates, phosphoramidates, and the like.

It will be understood that this invention is not limited to the particular nucleic acid sequences having sequence identifiers as listed in the SEQUENCE LISTING, but that functional equivalents known to one of skill in the art in light of this disclosure are also an aspect of the present invention.

Representative examples of useful oligonucleotides include nucleotides, oligonucleotides and polynucleotides primarily composed of adenine, cytosine, guanine, thymine or uracil bases. Non-standard bases, such as inosine or xanthine, are contemplated as well, as these may substitute for a standard base in some protocols, especially in hybridization protocols.

It will also be understood that bridging template nucleic acid molecules of the present invention may include additional nucleotides, such as additional 5' or 3' nucleotides, and yet still be essentially as set forth in one of the sequences disclosed herein, so long as the molecule meets the criteria set forth above, including the maintenance of bridging template activity.

Nucleic acid molecules that are "complementary" are those that are capable of base-pairing according to the standard Watson-Crick complementarity rules. As used herein, the term "complementary molecule" means a nucleic acid molecule that is substantially complementary, defined as being capable of hybridizing to a nucleic acid molecule under relatively stringent conditions such as those described herein in the detailed description of the preferred embodiments. Complementary nucleic acid molecules are useful for detection and purification of hybridizing nucleic acid molecules, and for antisense functions.

Hybridization Technology

An important aspect of the present invention is the ability of the bridging template nucleic acid molecules to anneal or hybridize to genomic DNA to form a sufficiently stable switch region duplex so that recombination may occur. The hybridization of nucleic acid molecules is well known in the art and depends upon salt concentration among other factors; generally, for molecules of less than about 50 nucleotides, a melting temperature for a hybrid is calculated as follows: # GC residues×4°+# AT residues×2°. This formula indicates that nucleic acid molecules having GC residues have a higher melting temperature than molecules rich in AT residues. Therefore, one may choose for a bridging template to be longer if it contains a large proportion of AT residues. Similarly, if a bridging template is rich in GC residues, it may not need to be as long to achieve hybridization.

The length of the nucleic acid molecule also influences the number of mismatches that would be allowed in a bridging template embodiment. For example, if 20, or 40 nucleotides were present both 3' and 5' to a "core" bridging template sequence, as many as 2–3 mismatches within the "core" sequence may be tolerated and still achieve hybridization stability sufficient for recombination to occur. Because of this relationship between length of molecule and tolerance of mismatches, sequences which have between about 70% and about 80%; or more preferably, between about 80% and about 90%; or even more preferably, between about 90% and about 99%; of nucleotides which are identical to the nucleotides of SEQ ID NO:1–16 are contemplated in the present invention.

Depending on the hybridization application envisioned, varying conditions of hybridization may be used to achieve varying degrees of selectivity of the bridging template towards target nucleic acid. For applications requiring high selectivity, relatively stringent conditions would be used to form the hybrids, e.g., relatively low salt and\or high temperature conditions, such as provided by 0.02M–0.15M NaCl at temperatures of 50° C. to 70° C. Such selective conditions tolerate little, if any, mismatch between the bridging template and the target nucleic acid molecule. Where functional equivalents, or the like, are employed, less stringent hybridization conditions may be needed in order to allow formation of a duplex or triplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. Generally, hybridization conditions may be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Sequences which are essentially the same as those set forth in SEQ ID NO: 1–16 may also be functionally defined as sequences which are capable of hybridizing to a nucleic acid segment containing the complement of said sequences under relatively stringent conditions. Suitable relatively stringent hybridization conditions will be well known to those of skill in the art and are clearly set forth herein, for example conditions for use with PCR, and as described in the examples.

Use of a bridging template of about 16 nucleotides in length allows the formation of a duplex molecule with genomic DNA that is both stable and selective. Molecules having complementary sequences over stretches greater than 16 bases would even further increase stability and selectivity of the duplex. Bridging template nucleic acid molecules having complementary stretches of 16 to 20, 25, 30, 35, 40, 50, or 75, or even up to the full length of an I exon and a C exon are yet other embodiments of the invention.

In certain embodiments, it will be advantageous to employ nucleic acid sequences of the present invention in combination with an appropriate indicator means, such as a label, for determining hybridization. A wide variety of appropriate indicator means are known in the art including fluorescent; radioactive; enzymatic such as urease, alkaline phosphatase, or peroxidase; or other ligands; such as avidin/biotin, which are capable of giving a detectable signal. In the case of enzyme tags, colorimetric indicator substrates are known which can be employed to provide a means visible to the human eye or spectrophotometrically, to identify specific hybridization with complementary nucleic acid-containing samples.

Nucleic acid molecules of the present invention may be combined with other DNA sequences, such as promoters, polyadenylation signals, additional restriction enzyme sites, multiple cloning sites, other coding segments, and the like, such that their overall length may vary considerably. It is contemplated that a nucleic acid molecule of almost any length may be employed, with the total length preferably being limited by the ease of preparation and use in the intended recombinant DNA protocol. For example, nucleic acid fragments may be prepared in accordance with the present invention which are up to 10,000 base pairs in length, such as segments of 5,000 or 3,000 and segments of about 1,000 base pairs in length.

Vectors and Host Cells

As used herein, the term "recombinant vector", refers to a vector that has been modified to contain a nucleic acid molecule of the present invention that is a sense molecule or an antisense molecule as defined herein, or functional equivalents thereof. The recombinant vector may be further defined as an expression vector comprising a promoter operatively linked to the sense or antisense nucleic acid molecule. The recombinant vector may also comprise further sequences such as expression control sequences, markers, amplifying genes, signal sequences, or the like.

Examples of promoters include the polyhedrin promoter, SV40 promoter, β-galactosidase promoter, and the like. By way of example and not limitation, vectors may be further defined as a pCMV (an example is provided herein as PBK-CMV), adenoviral, adeno-associated viral, retroviral, pUC and derivatives thereof, M13 and derivatives thereof, SV40, yeast plasmid, and the like.

A further aspect of the present invention is a host cell, made recombinant with a recombinant vector comprising a bridging template molecule or antisense nucleic acid molecule of the present invention. The recombinant host cell may be a prokaryotic or a eukaryotic cell. In a more preferred embodiment, the recombinant host cell is a eukaryotic cell. As used herein, the term "engineered" or "recombinant" cell is intended to refer to a cell into which a recombinant nucleic acid molecule of the present invention has been introduced. Therefore, engineered cells are distinguishable from naturally occurring cells which do not contain a recombinantly introduced nucleic acid molecule. Thus, engineered cells are cells having a nucleic acid sequence introduced through the hand of man. Recombinantly introduced nucleic acid sequences may be in the form of a cDNA (i.e., without introns), a copy of a genomic sequence, or may include nucleotide sequences positioned adjacent to a promoter not naturally associated with the particular introduced nucleic acid sequence, or combinations thereof. Exemplary host cells for nucleic acid molecules of the present invention include, but are not limited to primary B cells, or human B cell lines such as BL-2, JT or 2CA/F3, for example.

Ex vivo Treatment

Effective antisense retroviral vectors of the present invention may be transduced into stem cells obtained from a patient, and then these recombinant cells transplanted back into the patient. Hematopoietic stem cells can easily be removed from an individual, infected with antisense retroviral vectors, and then transplanted back to the same individual or to a suitable recipient by the technique of marrow transplantation.

Pharmaceutical Preparations

For the above-described uses, nucleic acid molecules are provided as pharmaceutical preparations. A pharmaceutical preparation of a nucleic acid molecule may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a nucleic acid molecule of the present invention and the pharmaceutically acceptable carriers are then easily administered in a variety of dosage forms. Administration may be intravenous, intraperitoneal, parenteral, intramuscular, subcutaneous, oral, or topical, with topical and intravenous administration being preferred, and intravenous being more preferred. Topical applications include inhalers or nasal sprays.

Solutions of the nucleic acid molecule in sterile aqueous medium may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Topical creams, emulsions, solutions, and the like are contemplated for applications to internal and external surface areas of the body, such as the respiratory and gastrointestinal mucosa and the skin. Topical application may also be by iontophoresis.

Excipients and preservatives that preserve oligonucleotide stability are preferred. The highly negatively charged phosphate or sulfur groups of the backbone of the oligonucleotide may be irritating to epithelial or other surface cells. Counterions may be used for formulation purposes to prevent irritation.

Pharmaceutical forms include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. Prolonged absorption of the injectable compositions can be brought about by the use in the compositions of agents delaying absorption, for example, aluminum monostearate and gelatin.

Sterile solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

IL-4 Induces Multiple Types of Chimeric Ig Germline Transcripts

IL-4 induces multiple types of Ig germline transcripts, including $\epsilon$, $\gamma 3$, $\gamma 1$ and $\gamma 4$ in humans (31,33). To determine whether Ig trans-spliced Ig mRNAs exist in human B cells, and whether IL-4 is also able to induce chimeric Ig mRNAs (i.e., Ig trans-mRNAs), RT-PCR methods were employed to amplify chimeric Ig germline transcripts with multiple sets of PCR primers derived from the human Ig loci (FIG. 1 and Tables 4 and 5).

Cells and Cell Cultures

Mononuclear cells were isolated from fresh human tonsil by Ficoll-Hypaque centrifugation depleted of adherent cells (26). Purified tonsillar B cells were negatively selected twice by depleting T cells with 2-aminoethylisothiouronium bromide-treated sheep red blood cells (Sigma, St. Louis, Mo.) (27). Purified B cells were greater than 95% $CD19^+$ cells and less than 1% $CD3^+$ cells (28). Resting B cells ($IgD^+B$ cells) were positively isolated by anti-human IgD mouse mAb (clone HB70 from ATCC, Rockville, Md.) and goat anti-mouse IgG coated magnetic beads (Dynal Great Neck, N.Y.) (31). This enriched population was 95% $IgD^+$ B cells and 4% $IgD^-$ B cells. The purification of this population was assessed by fluorescence analysis on FACScan (Becton Dickinson, Mountain View, Calif.). Purified B cells ($1 \times 10^6$ cells/ml) and $IgD^+$ B cells ($1 \times 10^6$ cells/ml) were cultured in RPMI medium supplemented with 2 mM glutamine, 10% FCS, 100 U/ml of penicillin and 100 µg/ml of streptomycin (complete medium) in the presence of IL-4 (200 U/ml, R and D Systems, Minneapolis, Minn.). CD40 mAb is from BioSource International (Camarillo, Calif.). GM1500 is a human EBV transformed cell line obtained from the National Institutes of General Medical Science (Camden, N.J.) (29).

RNA Extraction and Reverse Transcription

Total mRNA was obtained from stimulated and non-stimulated human B cells using Trizol reagent (Life Technologies, Gaithersburg, Md.) (30,31). The suspension of RNA was digested with DNase I (Sigma) to remove contaminating DNA, and then extracted with phenol/chloroform followed by precipitation of the RNA in ethanol. Two µg of total RNA was reverse-transcribed to cDNA using oligo $(dT)_{15}$ (Boehringer-Mannheim Co., Indianapolis, Ind.) as a primer and mouse Moloney leukemia virus reverse transcriptase (Life Technologies, Gaithersburg, Md.), as recommended by the manufacturer.

Isolation of Circular DNA and Genomic DNA

Switch circular DNA was prepared from the alkaline lysate of total cells (32). Precipitated circular DNA was treated with RNase for 2 hr at 37° C. to remove any remaining RNA, and then was used as a template for PCR. Genomic DNA was isolated by treatment with 0.1 M EDTA, 20 µg/ml of pancreatic RNase, 0.5% SDS, 10 mM Tris-HCl and proteinase K. After phenol-treatment, purified genomic DNA was digested with EcoRI to amplify Sµ/Sε fragment by PCR.

PCR Strategy

All PCR assays were run in a 50 µl/reaction with 50 mM KCl, 20 mM Tris-HCl (pH 8.4), 2.5 mM $MgCl_2$, 5% DMSO, 50 pM primer/reaction, and 2.5 U of Taq polymerase. For detection of γ2, γ4 and ε germline transcripts, γ2 productive transcripts and β actin, PCR reactions were carried out at 94° C. for 1 min, 65° C. for 1 min and 72° C. for 1 min for 40 cycles (FIG. 1, Table 4 and 5) (31, 33, 34).

Chimeric Ig germline transcripts were detected by nested primer PCR amplification (FIG. 1, Table 5). The first PCR was run under the same conditions as the PCR of each germline transcript except for the annealing temperature (60° C.). A second PCR was performed on a 5 µl aliquot of the first round PCR product and run at 94° C. for 1 min, 65° C. for 1 min and 72° C. for 1 min for 40 cycles. The primer sets employed for PCR are shown in Table 4 and their sequences are shown in Table 5. M1 was located in the beginning of the Iµ exon (35); M2 was in the beginning of µ switch region (36); G1, G2 and G3 were located in Iγ (36,37) while E1 and E2 were in the Iε region (33).

TABLE 4

Primer sets for PCRs employed in this study

| PCR fragment | First PCR | Second PCR |
|---|---|---|
| Germline transcript | | |
| γ2 | G1-CG3 | |
| γ4 | G1-CG1 | |
| ε | E1-CE2 | |
| µ | M1-CM2 | M1-CM1 |
| β actin | β1-β2 | |
| Productive transcript | | |
| γ2 | JH2-CG3 | |
| ε | JH2-CE2 | JH-CE2 |
| Chimeric RNA | | |
| Iµ-Cε | M1-CE2 | M1-CE0 |
| Iε-Cµ | E1-CM2 | E2-CM1 |
| IµCγ4 | M1-CG2 | M1-CG1 |
| Iγ4-Cµ | G1-CM2 | G2-CM1 |
| Iγ4-Cε | G1-CE2 | G2-CE1 |
| Iε-Cγ4 | E1-CG2 | E2-CG1 |
| Iε-Cγ2 | E1-CG4 | E2-CG3 |
| Iµ-Cγ2 | M1-CG4 | M1-CG3 |
| Circular DNA | | |
| Sγ/Sε | E3-SG2 | E5-SG1 |
| Interchromosomal DNA recombination | | |
| | E1-SG2 | E2-SG1 |
| | E1-SG4 | E2-SG3 |
| | E1-SG6 | E2-SG5 |
| | E3-SG2 | E4-SG1 |
| | E3-SG4 | E4-SG3 |
| | E3-SG6 | E4-SG5 |
| positive control | E3-E7 | E4-E6 |
| Sµ/Sε genomic DNA | M2-E9 | M2-E8 |

TABLE 5

Primer Oligonucleotide Sequences

| Name | Sequence | Ref | SEQ ID NO: | Name | Sequence | Ref | SEQ ID NO: |
|---|---|---|---|---|---|---|---|
| JH | TCGACTTCTGGGGCCAAGGG | 62 | 17 | JH2 | ACCCTGGTCACCGTCTCCTCA | 62 | 33 |
| M1 | ACAGTCTTAGGGAGAGTTTATGACTGT | 35 | 18 | M2 | ACAGTCTTAGGGAGAGTTTATGACTGT | 38 | 34 |
| G1 | GGGCTTCCAAGCCAACAGGGCACGACA | 34, 37 | 19 | G2 | TTGTCCAGGCCGGCAGCATCACCAGA | 34, 37 | 35 |
| G3 | TTGTCCAGGCCAGCAGCATCACTGGA | 34, 37 | 20 | SG1 | CTCTGGCCATCGGTGCCACCTCAG | 37 | 36 |
| SG3 | ACTGCTCAGTGGATGGACTCACACTCCCTT | 37 | 21 | SG4 | AAGCACACGTTCCTCCTGCAGCCACACCT | 37 | 37 |
| SG5 | TTGCCTATGTGCCCCTCCTGGATGA | 37 | 22 | SG6 | TTTTGCAGCACTTGGCTTGTTCCCTAT | 37 | 38 |
| CG1 | ATGGGCATGGGGGACCCATATTTGGA | 38, 63 | 23 | CG2 | ATGGTCCCCCCAGGAACTCAGGT | 38, 63 | 39 |
| CG3 | GTGGGCACTCGACACAACATTTGCG | 38, 63 | 24 | CG4 | ACTGACGGTCCTGCCACAGGTGGT | 38, 63 | 40 |

TABLE 5-continued

Primer Oligonucleotide Sequences

| Name | Sequence | Ref | SEQ ID NO: | Name | Sequence | Ref | SEQ ID NO: |
|---|---|---|---|---|---|---|---|
| CM1 | GACTGAAACCCGTGGCCTGGCAGATGA | 44 | 25 | CM2 | TCGCGCAGCCAGGACACCTGAATCT | 44 | 41 |
| E1 | AGGCTCCACTGCCCGGCACAGAAATA | 33 | 26 | E2 | AGCTGTCCAGGAACCCGACAGGGAG | 33 | 42 |
| E3 | AAGACCAAGAAGTCAGAGACCCGACTG | 36 | 27 | E4 | GCAGGGCTGGCTGGTGCAGACTGCC | 36 | 43 |
| E5 | TGTCCCTTAGAGGACAGGTGGCCAAG | 36 | 28 | E6 | CAGCTTAACTCAATCTGGACCACCA | 36 | 44 |
| E7 | CTGTGTCGGCCCAGCTTATTTCAACCAAG | 36 | 29 | E8 | CATCTCAGCTGAACCAGTTTGAC | 36 | 45 |
| E9 | TAGTGCGGTCTGTACAGCGTGGC | 36 | 30 | CE0 | ACGGAGGTGGCATTGGAGGGAATGT | 33 | 46 |
| CE1 | GTTGATAGTCCCTGGGGTGTA | 40 | 31 | CE2 | GGACAAGTCCACGTCCATGA | 40 | 47 |
| β1 | TCACCAACTGGGACGACATGGAG | 34 | 32 | β2 | CTCCTTAATGTCACGCACGATTTC | 34 | 48 |

Amplification of switch circular DNA and genomic Sμ/Sε switch junction employed nested primer PCRs (31, 32, 38). For the study of intrachromosomal DNA recombination, the same nested primer PCR strategy was employed as for chimeric germline transcripts except that different primer sets were used (Table 4).

Results

Amplified PCR products in purified IgD+ human B cells electrophoresed in 1% TBE-agarose gels demonstrated the following sized fragments corresponding to each chimeric germline mRNA: Iμ-Cε, 689 bp; Iε-Cμ, 497 bp; Iε-Cγ4, 393 bp; Iμ-Cγ4, 954 bp; Iγ4-Cμ, 511 bp; and Iγ4-Cε, 527 bp. In addition, chimeric Iγ4-Cα1 transcripts were also detected.

These chimeric germ-line transcripts were reproducibly detected in all samples of purified B cells stimulated with IL-4 alone from three sets of different tonsils. Such products were not detected in either unstimulated nor CD40 mAb-stimulated B cells. The size of the PCR products amplified was consistent with the expected size for the individual chimeric Ig germline transcript. Differential hybridization of these PCR products with corresponding I exon and C exon probes revealed that these PCR products were able to hybridize to the appropriate probes. These data support the finding by the present inventors that these PCR products are derived from the chimeric Ig mRNAs, indicating that IL-4 alone is able and sufficient to drive the production of the trans-spliced Ig germline RNA transcripts. As will be evident in Example 4 below, the ability to induce trans-spliced transcripts by IL-4 is a first step in isotype switching, the second step requires a second signal such as CD40 mAb stimulation, or in vivo, T cell stimulation, to accomplish switch recombination.

EXAMPLE 2

Sequence Analysis of the IL4-Induced Chimeric Trans-spliced Transcripts

The present example provides nucleotide sequences of the chimeric Ig germline trans-spliced mRNAs. The PCR products representing transcripts Iμ-Cε, Iε-Cμ, Iμ-Cγ4, Iγ4-Cμ, Iγ4-Cε, Iε-Cγ4 and Iγ4-Cα1 were subcloned and subjected to sequence analysis.

Cloning and DNA Sequencing of PCR Products

After gel electrophoresis of PCR products, samples were transferred to nylon membranes. Southern blots were hybridized with a [$^{32}$P]γATP end-labeled oligonucleotide probe PG (FIG. 1) corresponding to the γ4 CH1 region (TAGATCACAAGCCCAGCAACACCAAGGT, SEQ ID NO:74) (39) for Iε-Cγ4 chimeric transcripts, and with labeled probe PE (FIG. 1) corresponding to an εCH1 region (GCCTCCACACAGAGCCCATC, SEQ ID NO:75) (40) for Iγ-Cε chimeric transcripts according to standard methods (41).

The 5' SE fragment (1.2 kb), which was amplified from the E5 region to mid-Sε region by PCR (32), was labeled with [$^{32}$P]αCTP by random priming and hybridized to the membrane-bound PCR product for the study of switch circular DNA and intrachromosomal DNA recombination (FIG. 1).

The final PCR products were cloned using a TA cloning strategy (Invitrogen, San Diego, Calif.) (32). The inserts were excised from the cloning vectors by restriction endonuclease digestion (EcoRI, SalI, or ClaI), since the PCR amplified fragments have no EcoRI, SalI, or ClaI sites. Clones were then subjected to DNA sequence analysis. Nucleotide sequences were determined by the standard dideoxy chain termination method using a DNA sequencing kit (Sequenase version 2.0, Amersham, Arlington Heights, Ill.). T3, T7 and PCR primers were used as sequencing primers (31, 32).

Results

Nucleotide sequences at the splice junctions from cloned PCR products of trans-spliced chimeric Ig germline mRNAs for Iμ-Cε, Iε-Cμ, Iμ-Cγ4, Iγ4-Cμ, Iγ4-Cε, Iε-Cγ4 and Iγ4-Cα1 are shown below. The exon sequences are shown in italicized letters whereas the intron sequences are presented in regular print. The lines with the letter "g" represent the corresponding genomic DNA fragments. The nucleotide sequences of clones representing the trans-spliced RNA transcripts are aligned with the germline DNA sequences for determination of the splice junction.

```
Iμ-Cε      ----------Iμ--------------|
gIμ/Eμ     CAAGGCTCGCAGTGACCAGGCGCCCGACATGGTAAGAGACAGGCAGCCGCCGCTGCTGCA    SEQ. ID NO: 49
           ||||||||||||||||||||||||||||||
P12-15     CAAGGCTCGCAGTGACCAGGCGCCCGACATGCCTCCACACAGAGCCCATCCGTCTTCCCC    SEQ. ID NO: 50
                                         ||||||||||||||||||||||||||||||
gCHε       GGCTGGCACTGACTAGGTTCTGTCCTCACAGCCTCCACACAGAGCCCATCCGTCTTCCCC    SEQ. ID NO: 51
                                         |----------CHε--------------

Iε-Cμ-----------Iε-----------|
```

```
                                  -continued
gIε-Sε     AGGCACCAAATGGACGACCCGGCGCTTCAGGTATCCCAGCCCACCGGAGCCCCAATCGAG     SEQ. ID NO: 52
           ||||||||||||||  ||||||||||||||
P31-18     AGGCACCAAATGGACAGCCCGGCGCTTCAGGGAGTGCATCCAGCCCCAACCCTTTTCCCC     SEQ. ID NO: 53
                          ||||||||||  ||||||||||||||||||
gCHμ       CCCTTTCTCTTTTGTCCTGCGGGTCCTCAGGGAGTGCATCC-GCCCCAACCCTTTTCCCC     SEQ. ID NO: 54,55
                                     |---------Chμ1------------

Iγ4-Cμ     ------------Iγ4-----------|
gIγ4-Sγ4   CCTCCTCTCAGCCAGGACCAAGGACAGCAGGTGTGCCGGGAGCAGAGCAGCGAGGGTGAG     SEQ. ID NO: 56
           |||||||||||||||||||||||||||||
P165-2     CCTCCTCTCAGCCAGGACCAAGGACAGCAGGGAGTGCGTCCGCCCCAACCCTTTTCCACC     SEQ. ID NO: 57
                                          ||||||| |||||||||||||||||| ||
gCHμ       CCCTTTCTCTTTTGTCCTGCGGGTCCTCAGGGAGTGCATCCGCCCCAACCCTTTTCC-CC     SEQ. ID NO: 58
                                          |-----------CHμ1------------

Iμ-Cγ4     -------------Iμ--------------|
gIμ/Eμ     CAAGGCTCGCAGTGACCAGGCGCCCGACATGGTAAGAGACAGGCAGCCGCCGCTGCTGCA     SEQ. ID NO: 49
           |||||||||||||||||||||||||||||||
P26-2      CAAGGCTCGCAGTGACCAGGCGCCCGACATCTTCCACCAAGGGCCCATCCGTCTTCCCCC     SEQ. ID NO: 59
                                         |||||||||||||||||||||||||||||
gCHγ4      CGCGGTCACATGGCACCACCTCTCTTGCAGCTTCCACCAAGGGCCCATCCGTCTTCCCCC     SEQ. ID NO: 60
                                         |-------------CHγ4---------

Iε-Cγ4     ------------Iε------------|
gIε-Sε     AGGCACCAAATGGACGACCCGGCGCTTCAGGTATCCCAGCCCACCGGAGCCCCAATCGAG     SEQ. ID NO: 52
           |||||||||||||||||||||||||||
P112-1     AGGCACCAAATGGACGACCCGGCGCTTCAGCCTCCACCAAGGGCCCAT-CGTCTTCCCCC     SEQ. ID NO: 61,62
                                         | |||||||||||||||| |||||||||||
gCHγ4      CGCGGTCACATGGCACCACCTCTCTTGCAGCTTCCACCAAGGGCCCATCCGTCTTCCCCC     SEQ. ID NO: 60
                                         |-------------CHγ4---------
```

The sequences around the junctions revealed that the trans-splicing process utilized the same splicing donor and splicing acceptor consensus sequences in Iμ-Cε, Iε-Cμ, Iμ-Cγ4, Iγ4-Cμ, Iε-Cγ4 and Iγ4-Cα1 transcripts as for conventional Iμ-Cμ, Iγ4-Cγ4, Iε-Cε, and Iα1-Cα1 germline transcripts (I exons and CH1 exons). Such a splicing pattern for the generation of chimeric Ig mRNAs was confirmed in 4 independent studies with 3 individual sets of tonsils.

Two clones (P88-1 and P88-2) were chimeras of Iγ4 trans-spliced to Cε. These clones provided evidence for the Iγ4 exon being spliced correctly to the first exon of Cε. The difference between these two clones is the splice donor site in Iγ4; in clone P88-2 it was 25 nucleotides downstream of that in clone P88-1. The alternative use of the splice donor sites for chimeric Iγ4-Cε mRNA defined in clones P88-1 and P88-2 are below.

Only one splice donor site for γ germline transcripts has been reported in humans, the site found in clone P88-1 (37). In clone P88-2, the intronic 3' donor site splice sequence has the typical GU sequences and represents an alternative donor site. Alternative splice donor sites of the I exon have been reported for a germline transcripts (42).

A clone was also isolated representing Iγ4-Cα1 mRNA (clone P131-8) while assaying for Iγ4-Cε clones. This may have occurred because the antisense primer for Cε (CE1 and CE2) is homologous to part of α1CH2. This clone has the same characteristics as the other chimeric clones, the Iγ4 region is spliced to the first exon of CHα1.

```
                           2144
Iγ4-Cε     ----------Iγ4-------------↓
gIγ4-Sγ4   CCTCCTCTCAGCCAGGACCAAGGACAGCAGGTGTGCCGGGAGCAGAGCAGCGAGGGTGAG     SEQ. ID NO: 56
           |||||||||||||||||||||||||||||||
P88-1      CCTCCTCTCAGCCAGGACCAAGGACAGCAGCCTCCACACAGAGCCCATCCGTCTTCCCCT     SEQ. ID NO: 65
                                          ||||||||||||||||||||||||||||||
gCHε       GCTGGCACTGACTAGGTTCTGTCCTCACAGCCTCCACACAGAGCCCATCCGTCTTCCCCT     SEQ. ID NO: 66
                                          |-------------Chε----------

2144         2169
Iγ4-Cε     ----↓--------Iγ4-----------↓
gIγ4-Sγ4   AGCAGGTGTGCCGGGAGCAGAGCAGCGAGGGTGAGTGTGGCAGAGGACAGAAGGGTGGAA     SEQ. ID NO: 67
           |||||||||||||||||||||||||||||||
P88-2      AGCAGGTGTGCCGGGAGCAGAGCAGCGAGGCCTCCACACAGAGCCCATCCGTCTTCCCCT     SEQ. ID NO: 68
                                         ||||||||||||||||||||||||||||||
gCHε       GCTGGCACTGACTAGGTTCTGTCCTCACAGCCTCCACACAGAGCCCATCCGTCTTCCCCT     SEQ. ID NO: 69
                                         |------------CHε-----------
```

```
Iγ4-Cα1     ----------Iγ4-------------|
gIγ4-Sγ4    CCTCCTCTCAGCCAGGACCAAGGACAGCAGGTGTGCCGGGAGCAGAGCAGCGAGGGTGAG    SEQ. ID NO: 56
            ||||||||||||||||||||||||||||
P131-8      CCTCCTCTCAGCCAGGACCAAGGACAGCAGCATCCCCGACCAGCCCCAAGGTCTT---GC    SEQ. ID NO: 63
                               ||||||||||||||||||||||||||| ||
gCHα1       CGCGTCCTCACAGTGCATTCTGTGTTCCAGCATCCCCGACCAGCCCCAAGGTCTTCCCGC    SEQ. ID NO: 64
                                      |-------------CHα1------------
```

EXAMPLE 3

Semi-Quantitative Evaluation of Trans-spliced Iγ4-Cε and Iε-Cγ4 Germline Transcripts To estimate the amount of chimeric Ig germline transcripts induced by IL-4, a PCR based semi-quantitative method was developed to assay the frequency of chimeric Iγ4-Cε and Iε-Cγ4 germline transcripts. Plasmids containing cloned Iγ4-Cε and Iε-Cγ4 fragment (P88-1 and P112-1) were serially diluted and then subjected to PCR amplification. Semi-quantitative PCR assay was performed with 40 cycles of first round PCR and 15 cycles of second round PCR. One gram of plasmid DNA from each chimeric germ-line transcript was equivalent to $5.7 \times 10^{17}$ copies. The frequency of Iγ4-Cε chimeric germline transcripts derived from RNA (0.2 μg) of B cells stimulated with IL-4 (200 U/ml) alone for 7 days was determined to be $10^2$ to $10^3$ copies of template per reaction ($1.9 \times 10^{-4}$ to $1.9 \times 10^{-3}$ pg/μl). The amount of Iε-Cγ4 chimeric germline transcript from the same volume of RNA was 10 to $10^2$ copies per reaction ($1.9 \times 10^{-5}$ to $1.9 \times 10^{-4}$ pg/μl). Repeated PCR analyses of the same samples yielded similar results.

EXAMPLE 4

Mechanisms for Generation of Chimeric mRNA Transcripts

Possible mechanisms for generation of chimeric mRNA transcripts were examined including: i) trans-splicing of two discontinuous Ig pre-mRNA transcripts from unswitched B cells, ii) cis-splicing of Iμ containing transcripts driven from Ig heavy chain intronic enhancer/promoter (Iμ equivalent) from isotype-switched B cells, iii) cis-splicing of the chimeric pre-mRNA transcripts derived from switch circular DNAs resulting from isotype switch recombination, and iv) cis-splicing of the chimeric pre-mRNAs derived from Ig loci inter-chromosomal recombination.

Following IL-4 stimulation of highly purified IgM+, IgD+ B cells (containing 97% of surface IgD+ by FACS analysis), ε as well as γ3, γ1 and γ4 germline transcripts were induced, but Ig class switching was not induced since these IL-4 stimulated B cells only secreted IgM over a 10 day culture without detectable $IgG_{1-4}$, IgE or IgA when employing a highly sensitive ELISA with a lower limit of 10 pg/mL.

The inventors examined whether switch recombination had occurred. Southern blot analysis of PCR amplified Sε/Sγ switch circular DNA with 5' Sε probe demonstrated that the formation of switch circular DNAs was induced by IL-4 plus CD40 co-stimulation but not IL-4 alone. PCR generated fragments for Sε/Sγ switch circular DNA samples were hybridized with a 5'Sε probe (located in Sε region, see FIG. 1). Circular DNA as PCR templates was isolated from human B cells unstimulated and stimulated for 7 days. Positive bands (multiple) were only seen from IL-4 plus CD40 mAb-stimulated B cells. Therefore, using both amplification of circular DNA and analysis of genomic recombined switch fragments (31, 38), there was no molecular evidence that isotype switch recombination had occurred. In four studies with cells from four individual sets of tonsil cells stimulated with IL-4 alone, Sε/Sγ circular DNA was never detected.

Furthermore, if switch circular Iε-Sε/Sγ-Cγ DNA served as the template for generation of the chimeric Iε-Cγ4 mRNA, it would generate a chimeric germline pre-mRNA intermediate (Iε-Sε/Sγ-Cγ). Thus, the present inventors sought evidence for such pre-mRNA. Total RNA was extracted from human B cells after 7 days culture. Nested RT-PCR amplification was then performed to detect Iε-Sε/Sγ-Cγ pre-mRNA or Iε-Sε pre-mRNA. This shows an absence of Iε-Sε/Sγ-Cγ pre-mRNA hybridizing with the 5'Sε probe following PCR amplification by primer set E1-SG6 followed by primer set E2-SG5. As a positive control, Iε-Sε pre-mRNA (for ε germline transcript) was detected in RNA from IL-4 and IL-4 plus CD40 mAb-stimulated B cells employing primer set E3-E7 followed primer set E4-E6. The appearance of two positive bands resulted from the fact that a region highly homologous to the E4 primer exists in Sε-155 bp downstream of E4 site. In all, six nested PCR assays were performed employing 2 combinations of sense primers (E1-E2 and E3-E4) and 3 combinations of antisense primers (SG6-SG5, SG4-SG3 and SG2-SG1). No amplified fragments were found in any sample on agarose gels after six nested PCR's, nor were positive bands observed by Southern blot analysis using a 5'Sε probe. These results indicate that mechanisms involving cis-splicing of switched cells are unlikely operative in generating chimeric transcripts.

The sensitivity of this nested PCR assay for detection of chimeric pre-mRNA was assessed using a plasmid containing the Iε-Sε/Sγ-Cγ fragment which was obtained in the process of isolation of switch circular DNA resulting from γ to ε switching (32). This was serially diluted and then used as a template for PCR amplification. The primer set for the first round PCR was E1-SG2 and for second round was E2-SG1. One gram of this plasmid is equivalent to $4.9 \times 10^{17}$ copies of template. The Iε-Sε/Sγ-Cγ fragment consisted of 1020 base pairs. Between 1 to 10 copies of template could be amplified by the nested PCR. Thus, failure to amplify a pre-mRNA of chimeric germline transcripts was not due to poor sensitivity.

In summary, among the mechanisms herein described, only trans-splicing does not require some form of isotype switch recombination to occur. Multiple forms of chimeric Ig germline transcripts were detected from very highly purified resting B cells cultured with IL-4 alone, a stimulus known to induce ε, γ3, γ1, and γ4 germline transcripts but not to induce switch recombination. Studies failed to detect switch circular DNA, recombined genomic switch region fragments, or chimeric pre-mRNAs derived from transcription through recombined switch regions; suggesting that switch recombination did not occur in the IL4 stimulated B cells. Thus, trans-splicing of two independent (discontinuous) Ig pre-mRNA transcripts in unswitched B cells appears to be the mechanism for generation of chimeric Ig germline transcripts in IL-4 driven resting unswitched human B cells.

The present results show that IL-4 alone fails to induce switch recombination in purified resting B cells. IL4 is able to induce trans-splicing of transcripts, however, as stated in Example 1, a second signal is required for isotype switching, the second signal being CD40 or T cell stimulation. The data further support trans-splicing as the mechanism for the production of chimeric Ig transcripts.

EXAMPLE 5

Chimeric mRNAs from an IgG-Secreting Human Cell Line

Detection of multiple chimeric Ig germline transcripts in human B cells as identified by the present inventors led to the identification of trans-splicing between pre-mRNA of productive RNA transcripts (VDJ-$C\mu$,-VDJ-C$\gamma$, etc.) and that of $\gamma$ or $\epsilon$ germline transcripts (I$\gamma$-C$\gamma$, I$\epsilon$-C$\epsilon$, etc.). Such trans-splicing would produce productive transcripts and functional Ig isotypes without deletional recombination between two switch regions. However, $\epsilon$-productive transcripts detected in human purified B cells stimulated with IL-4 alone cannot be definitely shown to result from trans-splicing rather than from contamination by rare pre-switched B cells or from B cells switching in response to contamination by activated T cells. Therefore, the occurrence of chimeric mRNAs in an EBV transformed human B cell line, GM1500, which had undergone isotype switching, was investigated. For each analysis, the cells were stimulated for 7 days with IL-4 and/or $\alpha$CD40. Controls included purified human B cells and Raji cells cultured with IL4 plus CD40 mAb for 7 days. Raji cells are negative controls since they cannot switch and thus only produce one Ig isotype.

GM1500 cells produce IgG2 (29), express $\gamma$2 productive and $\epsilon$-germline transcripts, but not $\gamma$2 germline transcripts. Since the CH1 region of $\gamma$2 has a unique PvuII site, the $\gamma$-productive transcripts in GM1500 cells were shown as being $\gamma$2 by their pattern of restriction enzyme digestion (31). GM1500 expressed $\gamma$2 productive and $\epsilon$-germline transcripts, and this was enhanced by IL-4 plus CD40 mAb stimulation. Strikingly, $\epsilon$ productive transcripts were also amplified from unstimulated and stimulated GM1500 cells when a nested PCR was employed. The amplified fragment was identified as VDJ-C$\epsilon$ by cloning and DNA sequence analysis.

Trans-splicing between $\gamma$2 productive transcripts (VDJ-C$\gamma$2) and $\epsilon$ germline transcripts (I$\epsilon$-C$\epsilon$) should produce I$\epsilon$-C$\gamma$2 chimeric mRNAs in addition to $\epsilon$ productive transcripts (VDJ-C$\epsilon$). Indeed, the predicted 399 bp PCR I$\epsilon$-C$\gamma$2 chimeric fragment was amplified from GM1500 cells simulated with IL-4 alone or IL-4 plus CD40 mAb and its sequence was determined to represent I$\epsilon$-C$\gamma$2. These chimeric I$\epsilon$-C$\gamma$2 transcripts were generated by trans-splicing since no evidence was found that IL-4 plus anti-CD40 drove this EBV-transfected B cell line to switch from $\gamma$2 to $\epsilon$ locus., i.e. the study failed to identify S$\mu$/S$\epsilon$ switch fragments in genomic DNA of unstimulated and IL-4 plus CD40 mAb-stimulated GM1500 cells (38). As a positive control, fresh human B cells stimulated with IL-4 and CD40 mAb for 7 days yielded multiple switched fragments.

The S$\mu$/S$\gamma$ PCR assay was shown to detect between 1 to 10 copies of template containing S$\mu$/S$\epsilon$ junction. Consistent with these results, neither S$\gamma$2/S$\epsilon$ deleted switch circular DNAs nor I$\epsilon$-S$\epsilon$/S$\gamma$2-C$\gamma$2 pre-mRNA were detected in stimulated GM1500 cells.

EXAMPLE 6

Detection of IgE Protein in GM1500 Cells

Trans-splicing in GM1500 cells generated productive VDJ-C$\epsilon$ mRNA transcripts, transcripts that encode functional $\epsilon$ protein. To test whether IgE was produced, IgE production and surface IgE was measured on GM1500 cells. Measurement of IgE Production and Staining of IgE IgE levels in the supernatant of GM1500 cells were assessed by ELISA (28,29). A mixed two anti-human IgE (CIA-E-4.15 and CIA-E-7.12, Hassner, A. and Saxon, A., J. Immunol., 132:2844, 1984) were used as primary antibodies and alkaline phosphatase-labeled goat anti-human IgE was used for detection.

Cytoplasmic and surface IgE levels on GM1500 cells were assessed by using monoclonal anti-$\epsilon$ CIA-E-4.15 and CIA-E-7.12 following fixation with Permea-Fix (Ortho Diagnosis System, Raritan, N.J.), which allows detection of both membrane and cytoplasmic Ig. Following labeled anti-mouse Ig as a second reagent, cells were analyzed by flow cytometry. Positive cells were observed as dark brown under a microscope.

Immunohistochemical analysis of IgE in GM1500 cells was performed on slides where cytospin prepared cells were fixed in 95% ethanol:5% acetone (25). Slides were stained for cytoplasmic IgE using anti-$\epsilon$ CIA-E-4.15 and 7.12 antibodies followed by avidin biotin complex detection employing the Vectastain kit (Vector Laboratories, Burlingame, Calif.).

Results

U266-AF-10 cells (IgE producing plasma cell line) were essentially all positive. No IgE positive cells were observed in IgM+ Raji cells. Rare unstimulated GM1500 cells scored positive for cytoplasmic IgE, however, IgE could only be detected in GM1500 cells by histochemical staining. The frequency of positive cytoplasmic cells was <0.5%. IL-4 stimulation did not significantly enhance this. IgE was not detected by ELISA (sensitivity was 0.1 ng/ml) in the supernatant of GM1500 cells, nor did flow cytometric analysis, with its 2–3% sensitivity, detect surface or cytoplasmic IgE positive GM1500 cells.

EXAMPLE 7

Role of Sense and Antisense Trans-spliced Transcripts in Human Isotype Switch Recombination The present inventors contemplate use of trans-spliced chimeric transcripts provided herein as templates for effecting switch recombination and directing the specificity of Ig class switch recombination. Conversely, antisense transcripts are contemplated as inhibiting Ig class switch recombination.

Figure 2A:
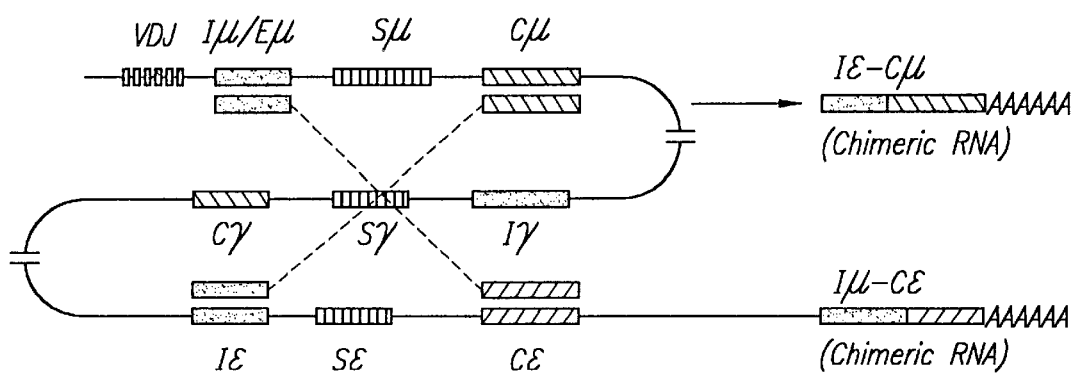
FIG. 2A shows generation of chimeric Ig germline transcripts through trans-splicing. The Iμ exon is trans-spliced to the Cε exon to generate the chimeric Iμ-Cε RNA transcript, while the Iε exon is reciprocally trans-spliced to the Cμ exon to generate the chimeric Iε-Cμ RNA transcript.
Figure 2B:
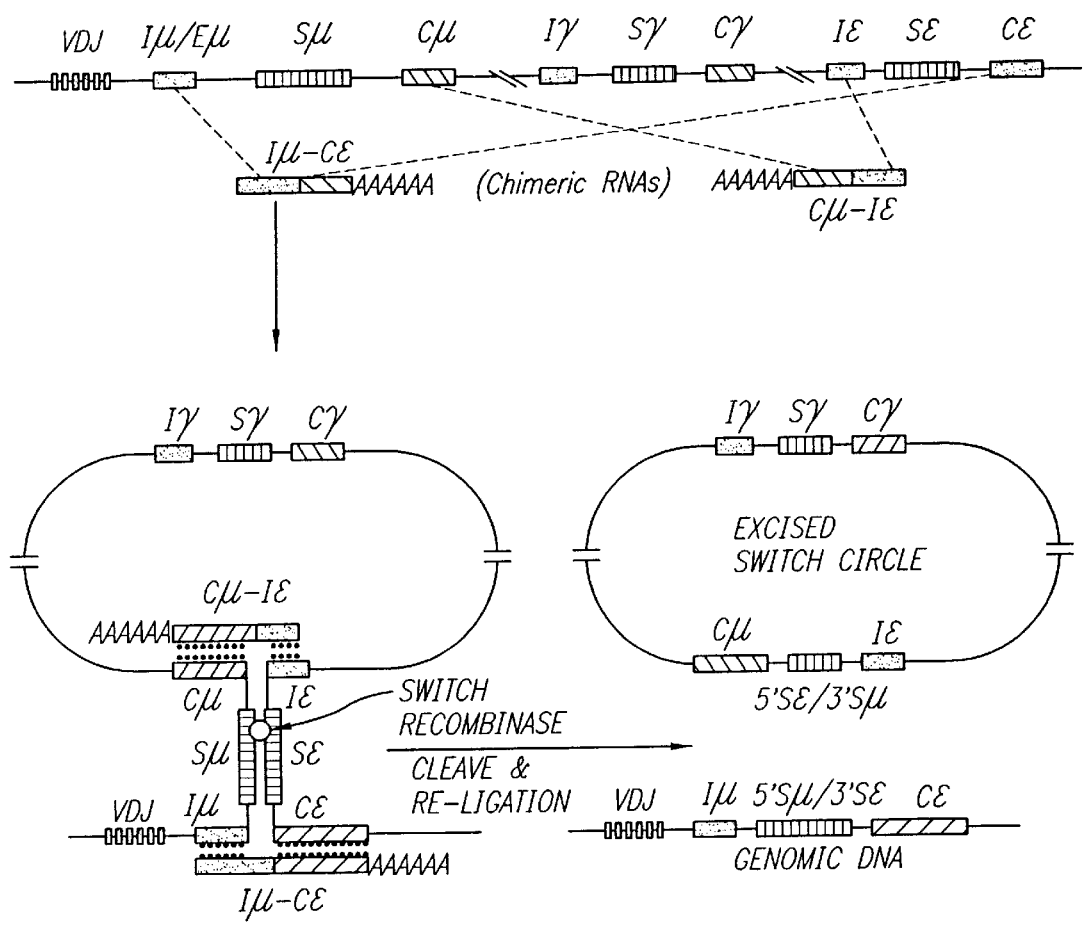
FIG. 2B shows a mechanism where chimeric Iε-Cμ and Iμ-Cε transcripts may determine the specificity of class switch recombination between Sμ and Sε. Single-stranded Iμ and Cε sequences of the trans-spliced mRNA's may base-pair to the double-stranded DNA of Iμ and Cε exons, respectively, in genomic DNA to function as a "bridging template." Iμ-Cε mRNA annealed to genomic DNA would bring 5' Sμ in close proximity to 3' Sε. Similarly, Iε-Cμ mRNA (shown upside down) may base pair to the double-stranded DNA of Iε and Cμ exons, respectively, and would bring the 3' Sμ in close proximity to 5' Sε as shown. This configuration allows the switch recombinase (shown as a circle) to access and catalyze the switch reaction. Intervening DNA would be deleted as a switch circle and the recombined DNA would then be present in the genome.

An example of an embodiment of the present invention is provided in FIG. 2A and FIG. 2B where trans-spliced transcripts having an I$\mu$-C$\epsilon$ structure would function as a "bridge" to bring 5' S$\mu$ in close proximity to 3' S$\epsilon$. The 5' portion of I$\mu$-C$\epsilon$ RNA is complementary to and would anneal to I$\mu$ region, while the 3' portion is complementary to and would anneal with the C$\epsilon$ exons (FIG. 2B). Similarly, I$\epsilon$-C$\mu$ chimeric transcripts resulting from trans-splicing could anneal with the I$\epsilon$ exon and the C$\mu$ exons on the DNA to be looped out (FIG. 2B). Such processes, by bringing together the two S regions, would facilitate catalytic recombination by the general Ig class switch recombinase.

In studying this embodiment, the effects of expression of chimeric native sense and chimeric anti-sense transcript constructs on induction of human isotype switch recombination will be examined. Sense sequences of I$\mu$-C$\epsilon$ and/or I$\epsilon$-C$\mu$ transcripts are expected to enhance S$\mu$-S$\epsilon$ switch recombination events. In contrast, the antisense sequences of I$\mu$-C$\epsilon$ and/or I$\epsilon$-C$\mu$ transcripts should specifically block or inhibit IL-4 plus CD40 induction of switch recombination between Sμ and Sε. In a similar manner, Iμ-Cγ and/or Iγ-Cμ constructs should only affect switch from μ to γ, with enhancement resulting from sense constructs, and inhibition occurring with antisense constructs.

Transfection and Switch Culture System

Separate constructs have been prepared in PBK-CMV plasmid containing Iμ-Cε, Iε-Cμ, Iμ-Cγ4, and Iγ4-Cμ trans-spliced fragments, each in both orientations. Highly purified resting human tonsillar B cells (IgM+ and IgD+) will be transfected with these constructs using electroporation. Corresponding Iμ, Iε, Iγ, Cμ, Cε, and Cγ fragments in PBK-CMV vector (Stratagene, San Diego, Calif.) will be used as controls. B cells will be cultured for 24 h during which time the anti-phOX single chain Ab will be expressed on the surface of transfected cells. The transfected anti-phOX positive B cells will be separated using magnetic beads coated with hapten phOX from non-transfected cells. Isolated B cells from each transfection group will be divided into four subgroups that will be cultured with i) medium alone, ii) IL-4 (100 U/ml), iii) CD40 mAb (0.1 μg/ml), and iv) IL-4 plus CD40 mAb for 5 and 14 days. At day 5, a portion of each group of cells will be harvested for DNA that will serve as a DNA template for Digested Circularization PCR (DC-PCR) assay to measure Sμ-Sε and Sμ-Sγ switch frequency. At day 14, Ig production will be assessed by specific ELISAs for IgE, IgM, and for the subclasses of IgG, and IgA.

Digested Circularization PCR (DC-PCR) Assay

The DC-PCR assay will be used to measure the level of Ig class switch recombination (Chu et al., *Proc. Nat'l. Acad. Sci.* 88:7528, 1992, incorporated by reference herein). For quantitating Sμ-Sε events, genomic DNA will be digested with BglII; for Sμ-Sγ switch, genomic DNA will be digested with HindIII. Following the circularization ligation processes, the resultant ligated DNA will be used as the DNA templates for PCR amplification. Appropriate internal controls will be generated for quantitation of each switch event.

Predicted Results

B cells stimulated with IL4 and CD40 mAb and transfected with Iμ-Cε and Iε-Cμ constructs in the sense orientation are expected to show enhanced Sμ-Sε but not Sμ-Sγ switch recombination. Similarly, stimulated B cells transfected with Iμ-Cγ and Iγ-Cμ constructs in the sense orientation are expected to show enhanced Sμ-Sγ but not Sμ-Sε switch recombination. In contrast, stimulated B cells transfected with Iμ-Cε and Iε-Cμ constructs in the anti-sense orientation are expected to be inhibited in Sμ-Sε but not Sμ-Sγ switch recombination while cells transfected with Iμ-Cγ and Iγ-Cμ antisense constructs are expected to specifically show inhibition of Sμ-Sε switch recombination. The corresponding control constructs are expected to have no effect on switch recombination. Theoretically, blocking γ switching could block ε class switching by inhibiting sequential switching via the γ genes. However, this will not be an obstacle since the present inventors have demonstrated direct switching between human μ and ε genes. Furthermore, in Sγ1 control region "knock out" mice, the frequency of ε switching was not affected even though γ 1 switch was completely blocked (Jung, et al., 1994, *J. Exp. Med.* 179:2023). Specific Ig protein levels may be decreased by control constructs with antisense Ig constant region gene sequences (i.e., Cμ, Cγ and Cε), since these antisense sequences may function as classic antisense RNAs and block translation of their corresponding productive Ig mRNAs. However, the control constructs will not affect switch recombination at the DNA level which will be assayed independently.

Study on Whether Reciprocal Pairs of Trans-spliced Transcripts Enhance Switch Recombination Whether reciprocal pairs of chimeric Ig germline transcripts are required or have synergistic effects on Ig switch recombination by cotransfection of two types of constructs will be studied. The effects on isotype switching of cotransfection of two reciprocal constructs in each orientation will be assessed as follows:

1) cotransfection of Iμ-Cε and Iε-Cμ constructs in sense orientation.
2) cotransfection of Iμ-Cε and Iε-Cμ constructs in antisense orientation.
3) cotransfection of Iμ-Cγ and Iγ-Cμ constructs in sense orientation.
4) cotransfection of Iμ-Cγ and Iγ-Cμ constructs in antisense orientation.

Pairs of the corresponding Iμ, Iε, Iγ, Cμ, Cε, and Cγ fragments in PBK-CMV in both orientations will be used as controls. Cultures and assays will be handled as described in the present example.

Predicted Results

Reciprocal pairs of chimeric Ig transcripts are expected to have enhanced effects on switch recombination compared with a single construct based on the expected synergistic effects of the two constructs binding to the DNA as in FIG. 2B and being able thereby to effect the same switch recombination event. Corresponding control fragments in PBK-CMV in both orientations are not expected to significantly affect switch recombination because they will not be able to bind to both regions as a single unit. Constructs containing antisense sequences may inhibit the corresponding Ig protein by functioning as classic antisense RNA which may inhibit the translation of the target isotype.

In summary, sense chimeric mRNA constructs are expected to specifically enhance corresponding isotype switch events and Ig production, while antisense constructs are expected to inhibit specific switching.

EXAMPLE 8

Ability of a 3'-5' Trans-spliced Transcript to Induce Primary Switch Recombination Analysis of the Ig switch circles revealed that primary switch recombination preferentially targets the 3' portion of donor S region and 5' portion of acceptor S regions. Similarly, secondary switch recombination preferentially targets the 5' end of donor S and 3' end of acceptor S regions and thereby provides for isotype stabilization. Based on the model presented in FIG. 2B, the trans-spliced Iε-Cμ chimeric Ig germline transcripts are likely to participate in recombination site selection for primary recombination, while Iμ-Cε transcripts direct secondary recombination site selection. In this recombination site selection model, prior to switch recombination, the trans-spliced Iε-Cμ transcripts bring the 3' end of Sμ in close proximity to the 5' end of Sε for primary switch recombination. Once primary switch recombination has occurred, the Cε gene is under the control of a VH promoter as well as the Eμ enhancer/Iμ promoter that constitutively transcribe the VDJ-Iμ-Sμ-Sε-Cε locus. This is known to produce Iμ-Cε transcripts through cis-splicing (Li, et al., 1994. *Int. Immunol.* 6:491) in addition to the more commonly recognized VDJ-Cε transcripts. These Iμ-Cε transcripts pair to the Iμ exon region and Cε exons, bringing the 5' end of Sμ in close proximity to 3' end of Sε to mediate the so-called "secondary deletion" which creates a recombination site with 5' Sµ sequence joined to the 3' end of Sε. To test whether Iε-Cµ and Iµ-Cε transcripts direct the selection for switch recombination sites corresponding to primary and secondary recombination respectively, the following constructs will be transfected or cotransfected into B cells.

1). Iε-Cµ vector in sense orientation.
2). Iε-Cµ vector in sense orientation and Iµ-Cε vector in antisense orientation.
3). Control vectors alone (PBK-CMV containing Iµ, Cµ, Iε, Cε fragments in sense orientation and pHook™).

Following 5 days culture with IL-4 and CD40 mAb, the B cells will be transformed by culture with EBV containing supernatants for 30 days. The "immortalized" B cells will then be cloned by limiting dilution to identify the IgE and IgG secreting cell lines as those that have undergone switch recombination. Genomic DNA from individual IgE and IgG cell lines will then be used as DNA templates for PCR to amplify the Sµ/Sε and Sµ/Sγ switch regions. The upstream primer will be located 5' to the beginning of Sµ and downstream primer will be located in the 3' to the end of Sε or Sγ. The amplified fragments will be cloned and sequenced to determine the exact switch recombination breakpoints. At the same time the genomic DNA will be digested with XbaI+BamH I (for Sµ/Sε switch) and XbaI+Hind III (for Sµ/Sγ switch) for Southern blot analysis and hybridized with either an Sµ or Sε/Sγ probe to determine the size of the switch fragments. If the transfected chimeric germline transcripts indeed facilitate the selection of the switch recombination sites, both PCR and Southern blot results should give the different sized pattern depending on where the switch recombination sites locate among the cell lines. The larger resultant fragments will be generated by switch recombination occurring close to 3' Sµ and/or 5' Sε (for E) or 5' Sγ (for γ). The smaller fragments will be generated by switch recombination occurring close to 5' Sµ and/or 3' Sε (for ε) or 3' Sγ (for γ). In order to avoid the possible bias, at least 20 clones from each group of cell lines will be analyzed.

Predicted Results

Expression of Iε-Cµ vector in sense orientation should greatly enhance the ability of endogenous trans-spliced Iε-Cµ transcripts to mediate recombination, resulting in primary recombination occurring between 3' part of Sµ and 5' part of Sε as is normally seen. Co-transfection of Iε-Cµ in sense orientation and Iµ-Cε vectors in antisense orientation would further increase the frequency of primary recombination events vs. secondary recombination as the antisense sequences of the Iµ-Cε transcripts would block the endogenous Iµ-Cε transcripts that are expected to mediate secondary recombination. Control plasmids should have no effect on the selection of switch recombination sites. Thus, the distribution of recombination sites from the control group B cells should represent the sites derived by the internal switch targeting machinery that will serve as an internal control. A potential pitfall for these studies is that the primary recombination effects mediated by Iε-Cµ vectors in sense orientation may be "masked" by subsequent dominant secondary recombination mediated by internally (naturally) derived Iµ-Cε transcripts after primary recombination has taken place. This would occur if the primary switched B cells have not been "immortalized" in time. However, there are two approaches to circumvent this, first is the use of the Iµ-Cε vector in antisense orientation that will block the natural Iµ-Cε transcripts. Furthermore, switched B cells may be transformed as early as day 3 if necessary to capture primary switched cells before they undergo secondary deletion.

EXAMPLE 9

Ability of a 5'-3' Trans-spliced Transcript to Induce Secondary Switch Recombination Analysis of Ig switch region structure from many stable isotype switched B cells reveals that the majority of the ultimate recombination sites are located at the 5' end or even upstream of the Sµ. These findings strongly contrast with results from switch circle analysis of primary switch recombination sites. The present inventors have demonstrated that secondary deletion within recombined chimeric S regions is a mechanism that can account for these differences. Without a secondary deletion/recombination mechanism, all B cells could continue to undergo sequential switching to the most distal isotype (IgA2 in humans). Consequently, secondary recombination/deletion is important in maintaining isotype production. In this sense, a balance between sequential switching and secondary recombination may be important in order to maintain an optimally isotype diverse humoral response. The following study will determine the role of chimeric Iµ-Cε transcripts in inducing switch recombination site selection characteristic of secondary recombination.

The present inventors will test whether Iµ-Cε transcripts mediate switch recombination occurring in 5' Sµ and 3' Sε as occurring during secondary recombination events. The following constructs will be transfected or co-transfected into B cells:

1). Iµ-Cε in a sense orientation.
2). Iµ-Cε in sense and Iε-Cµ in antisense orientation.
3). Control vectors alone (i.e., PBK-CMV containing Iµ, Cµ, Iε, Cε fragments in sense orientation and pHook™-1). After a 5 day culture with IL4 and CD40 mAb, transfected B cells will be transformed with EBV. The "immortalized" B cells will be cloned by limiting dilution to establish the switched IgE secreting cell lines as described in Example 10.

The nature and frequency of the switch recombination sites will be determined in the resulting IgE producing cells.

Overexpression of Iµ-Cε vector in sense orientation is expected to greatly enhance the frequency of primary switch recombination occurring between 5' Sµ and 3' Sε as compared with the control vectors wherein switch recombination is driven by the endogenous switch mechanism. The co-transfection of Iµ-Cε vectors in sense with Iε-Cµ in antisense orientation into B cells is predicted to further enhance the ability of transfected B cells to undergo primary switch recombination between 5' Sµ and 3' Sε recombination that occurs naturally in secondary deletion. Thus, transfected cells are expected to have a predominance of 5' Sµ and 3' Sε recombination sites, and chimeric RNAs such as Iµ-Cε likely direct this recombination.

EXAMPLE 10

Binding of Trans-spliced Transcripts to Transcriptionally Active Double-Stranded DNA According to the model of FIG. 2B, chimeric Ig germline transcripts anneal to the complementary region of the double stranded DNA to form a "triplex" DNA-RNA complex that lines up the two involved S regions for the switch region DNA recombination. This theory of complex formation is supported by the evidence that single stranded RNA and DNA can pair in a stable manner with the complementary region of the double stranded DNA through Hoogsteen base-pair formation rather than Watson-Crick base-pair formation. To examine whether chimeric Ig germline transcripts (RNA) can form a three-stranded synaptic complex with double stranded DNA through the mechanism of Hoogsteen base-pair formation, the following study will be performed. This will demonstrate the existence of the hetero-triplex DNA-RNA complex and whether the chimeric Ig germline mRNAs can anneal to the complementary region of the double stranded DNA.

The ε-γ4 chimeric construct will be used as a double stranded DNA template to test whether chimeric Iε-Cγ4 germline mRNA transcripts can anneal to transcriptionally active vs inactive double stranded DNA to form a triplet complex in vitro. The ε-γ4 chimeric construct was derived from the "ε and γ4 structures" described herein by replacing Iγ and its 3' flanking sequences in the γ construct with Iε and its 5' flanking sequences from the ε structure. This double stranded ε-γ4 DNA construct will be incubated with $^{32}P$ labeled chimeric Iε-Cγ4 germline RNA transcripts derived from in vitro transcription of cloned Iε-Cγ4 cDNA in PBK-CMV. The reaction will be incubated at 37° C. to detect and determine the kinetics of the proposed 2:1 DNA-RNA triplet formation. The resultant products will be resolved in 3% polyacrylamide gels or 0.9% agarose gels. If Iε-Cγ4 RNA germline transcripts specifically associate with the template DNA, the radioactivity will migrate with template DNA, otherwise the labeled RNA will only appear at the gel front. As controls, the labeled chimeric RNA will be replaced with a similar sized noncomplementary $^{32}P$ labeled RNA. Non-complementary plasmid DNA incubated with labeled Iε-Cγ4 RNA transcripts will also be employed.

To assess whether transcriptional activity is required for the formation of the 2:1 DNA-RNA triplet, the ε-γ4 chimeric DNA constructs will be treated with T3 RNA polymerase to induce transcriptional activation. These transcriptional active DNA constructs will be incubated with the $^{32}P$ labeled Iε-Cγ4 germline transcripts RNAs and compared to the results obtained with DNA constructs prepared without T3 RNA polymerase.

Iε-Cγ4 RNA is expected to pair to the corresponding complementary region in the DNA constructs through Hoogsteen base-pair formation mechanism. If the outcome is as expected, it will be further examined whether both parts of the Iε-Cγ4 RNA transcripts (i.e., Iε sequence and Cγ4 sequence independently) would pair to the corresponding region.

EXAMPLE 11

Nucleic Acid Molecule Analogs for Protection Against In Vivo Degradation

Oligonucleotides have several advantages over traditional drugs, notably their exquisite specificity to target sites and their ease of design. Oligonucleotides may be derivatized at the bases, the sugars, the ends of the chains, or at the phosphate groups of the backbone to promote in vivo stability. CpG sequences may be derivatized to minimize degradation; derivatization may be alkylation, and is preferably methylation. Modifications of the phosphate groups are preferred in one embodiment of the invention since phosphate linkages are sensitive to nuclease activity. Preferred derivatives are the methylphosphonates, phosphotriesters, phosphorothioates, and phosphoramidates. Derivatives may also contain alternating phosphorothioate and unmodified linkages, or alternating methylphosphonate and unmodified linkages, or alternating phosphorothioate and methylphosphonate linkages. Additionally, the phosphate linkages may be completely substituted with non-phosphate linkages such as amide linkages. Appendages to the ends of the oligonucleotide chains also provide exonuclease resistance. The 5' or 3' end may be derivatized or "capped" with a phosphoramidate linkage, an inverted nucleotide conjugated to the oligonucleotide via a 3'—3' linkage, an aminoacridine residue, or poly-L-Lysine.

Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl. The O-methylation derivatization serves to protect the ribonucleotide from degradation.

The terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like.

An exemplary method for delivering oligonucleotides into a cell is the use of glycoconjugates for carrying oligonucleotides specific for targeted sequences. Oligonucleotides protected at both ends and linked through a disulfide bridge to a glycoconjugate are significantly more effective in reaching a target site than the corresponding free oligonucleotides. Poly-L-lysine can be substituted by three components: a sugar as a recognition signal, an active oligonucleotide element, and gluconoic acid as a neutralizing and solubilizing agent. This type of neutral, highly water-soluble glycosylated polymer is an efficient carrier to deliver drugs into cells according to the nature of the sugar attached to the polymer.

For general reviews of synthesis of DNA, RNA, and their analogues, see *Oligonucleotides and Analogues*, F. Eckstein, Ed., 1991, IRL Press, New York; *Oligonucleotide Synthesis*, M. J. Gait, Ed., 1984, IRL Press Oxford, England; Caracciolo et al. (1989); *Bioconjugate Chemistry*, Goodchild, J. (1990); or for phosphonate synthesis, Matteucci, MD. et al., *Nucleic Acids Res.* 14:5399 (1986) (the references are incorporated by reference herein). Preferred oligonucleotides resistant to in vivo hydrolysis may contain a phosphorothioate substitution at each base (*J. Org. Chem.*, 55:4693–4699, (1990)).

In general, there are three commonly used solid phase-based approaches to the synthesis of oligonucleotides containing conventional 5'-3' linkages. These are the phosphoramidite method, the phosphonate method, and the triester method.

A brief description of a current method used commercially to synthesize oligomeric DNA is as follows: Oligomers up to ca. 100 residues in length are prepared on a commercial synthesizer, e.g., Applied Biosystems Inc. Model 392 (Applied Biosystems, Inc., Foster City, Calif.) that uses phosphoramidite chemistry. DNA is synthesized from the 3' to the 5' direction through the sequential addition of highly reactive phosphorous(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add a further residue until the desired DNA polymer is synthesized. The full length polymer is released from the solid support, with concomitant removal of remaining protective groups, by exposure to base. A common protocol uses saturated ethanolic ammonia.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete. The phosphonates can also be converted to phosphoramidate derivatives by reaction with a primary or secondary amine in the presence of carbon tetrachloride.

In the triester synthesis, a protected phosphodiester nucleotide is condensed with the free hydroxyl of a growing nucleotide chain derivatized to a solid support in the presence of coupling agent. The reaction yields a protected phosphate linkage which may be treated with an oximate solution to form unprotected oligonucleotide.

To indicate the three approaches generically, the incoming nucleotide is regarded as having an "activated" phosphite/phosphate group. In addition to employing commonly used solid phase synthesis techniques, oligonucleotides may also be synthesized using solution phase methods such as diester synthesis. The methods are workable, but in general, less efficient for oligonucleotides of any substantial length.

For antisense applications, excipients and preservatives that preserve oligonucleotide stability are chosen. The highly negatively charged phosphate or sulfur groups of the backbone of the oligonucleotide may be irritating to epithelial or other surface cells. Counterions may be used for formulation purposes to prevent irritation. Antisense technology is discussed in U.S. Pat. Nos. 5,194,428, 5,110,802 and 5,216,141, all of which are incorporated by reference herein.

Nucleic acid molecules of the present invention may also be obtained by application of nucleic acid reproduction technology, such as the PCR technology of U.S. Pat. No. 4,683,202 (herein incorporated by reference).

EXAMPLE 12

Delivery of Nucleic Acid Molecules via in Vivo Expression

This prophetic example describes some of the ways in which sense or antisense nucleic acid molecules of the present invention may be introduced into lymphoid cells, in particular, into primary B cells. There are numerous ways for introducing a donor DNA or RNA into target cells (cells that receive targeted integration) including electroporation, microinjection, calcium phosphate coprecipitation, liposome-based membrane fusion, and use of retroviral or adenoviral vectors.

A preferred method for in vivo delivery of nucleic acid agents of the present invention is by transcription from a vector encoding the particular nucleic acid molecule so that the agent is endogenously expressed. A vector may be an adenoviral vector, an adeno-associated vector, a retroviral vector, a herpes vector, or the like, all such vectors having been modified so as to be noninfectious on their own.

Human adenoviruses are a means for introducing nucleic acid molecules into tissue. Adenoviruses are double-stranded DNA tumor viruses with genome sizes of approximately 36 kb. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Adenoviruses deleted in both E1 and E3 regions are capable of carrying up to 10 kb of foreign DNA and can be grown to high titers. Persistent expression of transgenes follows adenoviral infection.

Particular advantages of an adenovirus system for delivering foreign genes and to a cell include (i) the ability to substitute relatively large pieces of viral DNA with foreign DNA; (ii) the structural stability of recombinant adenoviruses; (iii) the safety of adenoviral administration to humans; (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Human subjects for whom medical indication for adenovirus-mediated gene transfer of a nucleic acid molecule affecting immunoglobulin isotype switching has been established would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus providing nucleic acid molecules of the present invention is prepared and purified by any method that would be acceptable to the Food and Drug Administration for administration to human subjects, including, but not limited to, cesium chloride density gradient centrifugation, and subsequently tested for efficacy and purity. Virus is administered to patients by means of intravenous injection, or administration to lymphoid cells via bone marrow in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

For plasmid-directed synthesis of the nucleic acid molecules of the present invention, poly-L-lysine partially substituted with sugars is a polycationic glycosylated polymer that makes complexes with plasmids and enhances uptake of plasmid DNA. Expression of reporter genes is enhanced when cells are incubated with the plasmid-glycosylated poly-L-lysine complex in the presence of either 100 µM chloroquine or 10 µM fusogenic docosapeptide.

Transduction of infectious, replication-defective retroviruses containing sense or antisense nucleic acid molecules of the present invention into a packaging cell line is another method for producing virus for in vivo delivery.

Many cell lines, known to one of skill in this art in light of this disclosure, contain viral functions necessary for packaging and delivery of replication-defective viral vectors derived from several commonly used tumor viruses. These useful viruses include MLV, spleen necrosis virus (SNV), avian leukosis virus (ALV), and reticuloendotheliosis virus (REV). Patents have issued for helper cell lines for MLV and REV (Miller, U.S. Pat. No. 4,861,719; Temin et al., U.S. Pat. No. 4,650,764). MLV vector systems have been approved for limited human gene therapy trials. U.S. Pat. No. 5,399,346 to Anderson et al. is incorporated by reference herein as teaching gene therapy techniques, particularly methods whereby primary human cells are genetically engineered with DNA (RNA) encoding a therapeutic which is to be expressed in vivo.

EXAMPLE 13

Liposome Delivery of Nucleic Acid Molecules

The present example outlines a method that may be used to associate the nucleic acid molecules of the present invention with liposomes. These liposome preparations will then be used to determine their effects on isotype switching in unswitched immunoglobulin-producing cells. Encapsulation in liposomes would improve biological stability and improve cellular uptake especially when the oligonucleotide is conjugated to a lipophile such as cholesterol or a lipid. Efflux from endosomes may be effected by using pH-sensitive liposomes, or oligonucleotide conjugates with membrane destabilizers. Sustained release formulations would enhance activity against targets with slow turnover.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the nucleic acid molecules. They are widely suitable since both water- and lipid-soluble substances can be entrapped in the aqueous spaces and within the bilayer itself, respectively. It is possible that drug-bearing liposomes may even be employed for site-specific delivery of active agents by selectively modifying the liposomal formulation.

The formation and use of liposomes is generally known to those of skill in the art. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical property of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via a number of different mechanisms including: endocytosis by phagocytic cells of the reticuloendothelial system such as macrophages and neutrophils; adsorption to the cell surface, either by non-specific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface, such as an unswitched B cell, for example. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Esser, C. and A. Radbruch. 1990. *Annu. Rev. Immunol.* 8:717.
2. Stavnezer-Nordgren, J., and S. Sirlin. 1986. *EMBO. J* 5:95.
3. Lutzker, S., and F. W. Alt. 1988. *Mol. Cell. Biol.* 8:1849.
4. Radcliffe, G., et al. 1990. *Mol. Cell. Biol.* 10:382.
5. Rothman, P., et al. 1990. *Mol. Cell. Biol.* 10:1672.
6. Lutzker, S., et al. 1988. *Cell.* 53:177.
7. Stevnezer, J., et al. 1988. *Proc. Natl. Acad. Sci. USA.* 85:7704.
8. Lorenz, M., et al. 1995. *Science.* 267:1825.
9. Jung, S., et al. 1993. *Science.* 259:984.
10. Zhang, J., et al. 1993. *EMBO J.* 12:3529.
11. Xu, L., et al. 1993. *Proc. Natl. Acad. Sci. USA.* 90:3705.
12. Bottaro, A., et al. 1994. *EMBO J.* 13:665.
13. Harriman, G. R., et al. 1996. *J. Clin. Invest.* 97:477.
14. Shimizu, A., et al. 1989. *Proc. Natl. Acad. Sci. USA.* 86:8020.
15. Shimizu, A., et al. 1991. *J. Exp. Med.* 173:1385.
16. Han, H., et al. 1991. *Int. Immunol.* 12:1197.
17. Shimizu, A., and T. Honjo. 1993. *FASEB J.* 7:149.
18. Yaoita, Y., et al. 1982. *Nature.* 297:697.
19. Perlmutter, A. P., and W. Gilbert. 1984. *Proc. Natl. Acad. Sci. USA.* 81:7189.
20. Chen, Y. W., et al. 1986. *J. Exp. Med.* 164:562.
21. Kinashi, T., et al. 1987. *Genes. Dev.* 1:465.
22. Nolan-Willard, M., et al. 1992. *Proc. Natl. Acad. Sci. USA.* 89:1234.
23. Kunimoto, D. Y., et al. 1993. *J. Immunol.* 150:1338.
24. Mackenzie, T., and H. M. Dosch. 1989. *J. Exp. Med.* 169:407.
25. Chan, M. A., et al. 1990. *J. Immunol.* 144:3563.
26. Fujieda, S., et al. 1994. *Arch. Otolaryngol. Head Neck Surg.* 120:389.
27. Saxon, A., et al. 1976. *J. Immunol. Methods.* 12:285.
28. Zhang, K., et al. 1991. *J. Immunol.* 146:1836.
29. Sherr, E., et al. 1989. *J. Immunol.* 142:481.
30. Chomczynski, P., and N. Sacchi. 1987. *Anal. Biochem.* 162:156.
31. Fujieda, S., et al. 1995. *J. Immunol.* 155:2318.
32. Zhang, K., et al. 1994. *J. Immunol.* 152:3427.
33. Gauchat, J. F., et al. 1990. *J. Exp. Med.* 172:463.
34. Diaz-Sanchez, D., et al. 1994. *J. Clin. Invest.* 94:1417.
35. Neale, G. G. A. M., and G. R. Kitchingman. 1991. *Nucl. Acids Res.* 19:2427.
36. Mills, F. C., et al. 1990. *Nucleic Acids Res.* 18:7305.
37. Sideras, P., et al. 1989. *Int Immunol.* 1:631.
38. Shapira, S. K., et al. 1991. *Proc. Natl. Acad. Sci. USA.* 88:7528.
39. Ellison, J., and L. Hood. 1982. *Proc. Natl. Acad. Sci. USA.* 79;1984.
40. Max, E. E., et al. 1982. *Cell.* 29:691.
41. Zhang, K., et al. 1992. *J. Exp. Med.* 176:233.
42. Graff, C, and S. Gerondakis. 1990. *Int. Immunol.* 2:1143.
43. Li, S. C., et al. 1994. *Int. Immunol.* 6:491.
44. Gerstein, R. M., et al. 1990. *Cell.* 63;537.
45. Knight, K. L., et al. 1995. *J. Immunol.* 155:684.
46. Murphy, W. J., et al. 1986. *Cell.* 47:517.
47. Sutton, R. E., and J. C. Boothroyd. 1986. *Cell.* 47:527.
48. Borst, P. 1986. *Ann. Rev. Biochem.* 55:701.
49. Nilsen, T. W. 1993. *Annu. Rev. Microbiol.* 47:413.
50. Solnick, D. 1985. *Cell.* 42:157
51. Zaita, N., et al. 1987. *FEBS Lett.* 210:153.
52. Koller, B., et al. 1987. *Cell.* 48:111.
53. Sen, D., and W. Gilbert. 1990. *Nature* 344:410.
54. Kim J., et al. 1991. *Nature* 351:331.
55. Cheong, C., and P. B. Moore. 1992. *Biochemistry.* 31:8406.
56. Chiara M. D., and R. Reed. 1995. *Nature* 375:510.
57. Sklenar, V., and J., Feigon. 1990. *Nature.* 345:836.
58. Kim, M. G., et al. 1995. *J. Mol. Biol.* 247:874.
59. Van Meervelt, L., et al. 1995. *Nature.* 374:742.
60. Zhurkin, V. B., et al. 1994. *J. Mol. Biol.* 239:181.
61. Morgan, A. R. 1994. *Indian J. Biochem. & Biophysics.* 31:83.
62. Ravetch, J. V., et al. 1981. *Cell* 27:583.
63. Kitani, A., and W. Strober. 1993. *J. Immunol.* 151:3478.

What is claimed is:

1. A purified nucleic acid molecule having a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15.

2. A purified nucleic acid molecule having a nucleotide sequence of SEQ ID NO: 50, SEQ ID NO: 53, SEQ ID NO: 57, SEQ ID NO: 59, SEQ ID NO: 61, SEQ ID NO: 63, SEQ ID NO: 65, or SEQ ID NO: 68.

3. A purified nucleic acid molecule complementary to the nucleic acid molecule of claim 1 or 2.

4. The purified nucleic acid molecule of claim 3 having a nucleotide sequence of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16.

5. A recombinant vector comprising the purified nucleic acid molecule of claim 1, 2 or 4.

* * * * *